US011345554B2

(12) United States Patent
Shea et al.

(10) Patent No.: US 11,345,554 B2
(45) Date of Patent: May 31, 2022

(54) METHOD AND APPARATUS FOR FLEXIBLY ASSEMBLING PACKAGES OF ABSORBENT ARTICLES

(71) Applicant: The Procter & Gamble Company, Cincinnati, OH (US)

(72) Inventors: Paul Shea, Belleville (CA); Darryll Joseph Weil, II, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 250 days.

(21) Appl. No.: 16/377,365

(22) Filed: Apr. 8, 2019

(65) Prior Publication Data

US 2019/0307614 A1    Oct. 10, 2019

Related U.S. Application Data

(60) Provisional application No. 62/655,266, filed on Apr. 10, 2018.

(51) Int. Cl.
*A61F 13/551* (2006.01)
*B65G 54/02* (2006.01)
(Continued)

(52) U.S. Cl.
CPC .......... *B65G 54/02* (2013.01); *A61F 13/5514* (2013.01); *A61F 13/5519* (2013.01);
(Continued)

(58) Field of Classification Search
CPC .................. A61F 13/5514; A61F 13/62; A61F 13/55105; A61F 13/1565; B65G 47/082; B65B 35/30; B65B 2210/02; B65B 65/003
(Continued)

(56) References Cited

U.S. PATENT DOCUMENTS 3,771,679 A    11/1973  Theml
3,803,466 A     4/1974  Starkey
(Continued)

FOREIGN PATENT DOCUMENTS

EP    1127791 A1    8/2001
EP    1278691 B1   12/2004
(Continued)

OTHER PUBLICATIONS

PCT International Search Report, dated Jul. 10, 2019, 15 pages.

*Primary Examiner* — Robert F Long
*Assistant Examiner* — Xavier A Madison
(74) *Attorney, Agent, or Firm* — Jay A. Krebs; Charles R. Matson

(57) ABSTRACT

Apparatuses and methods herein may be configured to utilize existing high speed assembly lines with dedicated packaging apparatuses to assemble various kinds of packages of absorbent articles. Absorbent articles advancing from an assembly line are diverted before reaching a dedicated packaging apparatus. The diverted absorbent articles are transported to a selectable packaging apparatus to be placed in containers containing desired quantities and/or types of absorbent articles to create select packages. Carriers are movably connected with a track, wherein a linear synchronous motor independently moves the carriers along the track. Diverted absorbent articles are transferred to a carrier in a receiving zone, and the diverted absorbent articles are moved along the track from the receiving zone to a drop off zone. The diverted absorbent articles are then transferred from the carrier in the drop off zone to a selectable packaging apparatus.

20 Claims, 12 Drawing Sheets

(51) Int. Cl.
*B65G 37/02* (2006.01)
*B65G 47/08* (2006.01)
*B65B 65/00* (2006.01)
*B65B 35/30* (2006.01)
*A61F 13/15* (2006.01)
*A61F 13/62* (2006.01)

(52) U.S. Cl.
CPC ........ *A61F 13/55105* (2013.01); *B65B 35/30* (2013.01); *B65B 65/003* (2013.01); *B65G 37/02* (2013.01); *B65G 47/082* (2013.01); *A61F 13/1565* (2013.01); *A61F 13/15699* (2013.01); *A61F 13/15707* (2013.01); *A61F 13/62* (2013.01); *B65B 2210/02* (2013.01)

(58) Field of Classification Search
USPC .......................................................... 53/443
See application file for complete search history.

(56) References Cited

U.S. PATENT DOCUMENTS

| | | |
|---|---|---|
| 4,114,538 A | 9/1978 | Nicodemus, Jr. et al. |
| 4,324,246 A | 4/1982 | Mullane et al. |
| 4,342,314 A | 8/1982 | Radel et al. |
| 4,463,045 A | 7/1984 | Ahr et al. |
| 4,556,146 A | 12/1985 | Swanson et al. |
| 4,589,876 A | 5/1986 | Van Tilburg |
| 4,687,478 A | 8/1987 | Van Tilburg |
| 4,940,464 A | 7/1990 | Van Gompel et al. |
| 4,950,264 A | 8/1990 | Osborn, III |
| 5,009,653 A | 4/1991 | Osborn, III |
| 5,092,861 A | 3/1992 | Nomura et al. |
| 5,135,102 A | 8/1992 | Sjogren et al. |
| 5,167,897 A | 12/1992 | Weber et al. |
| 5,246,433 A | 9/1993 | Hasse et al. |
| 5,267,992 A | 12/1993 | Van Tilburg |
| 5,360,420 A | 11/1994 | Cook et al. |
| 5,388,706 A | 2/1995 | Baldur |
| 5,450,939 A | 9/1995 | Meyers et al. |
| 5,569,228 A | 10/1996 | Byrd et al. |
| 5,569,234 A | 10/1996 | Buell et al. |
| 5,599,335 A | 2/1997 | Goldman et al. |
| 5,643,588 A | 7/1997 | Roe et al. |
| 5,674,216 A | 10/1997 | Buell et al. |
| 5,702,551 A | 12/1997 | Huber et al. |
| 5,842,556 A | 12/1998 | van Hattum |
| 5,897,542 A | 4/1999 | Lash et al. |
| 5,897,545 A | 4/1999 | Kline et al. |
| 5,957,908 A | 9/1999 | Kline et al. |
| 5,968,025 A | 10/1999 | Roe et al. |
| 5,996,316 A * | 12/1999 | Kirschner ............ B65G 1/1378 |
| | | 53/155 |
| 6,004,893 A | 12/1999 | Van Tilburg |
| 6,074,376 A | 6/2000 | Mills |
| 6,104,966 A | 8/2000 | Haagensen |
| 6,107,537 A | 8/2000 | Elder et al. |
| 6,118,041 A | 9/2000 | Roe et al. |
| 6,120,487 A | 9/2000 | Ashton |
| 6,120,489 A | 9/2000 | Johnson et al. |
| 6,153,209 A | 11/2000 | Vega et al. |
| 6,298,975 B1 | 10/2001 | Fortenbery et al. |
| 6,318,555 B1 | 11/2001 | Kuske et al. |
| 6,410,129 B2 | 6/2002 | Zhang et al. |
| 6,426,444 B2 | 7/2002 | Roe et al. |
| 6,454,095 B1 | 9/2002 | Brisebois et al. |
| 6,510,799 B2 | 1/2003 | Lamb et al. |
| 6,586,652 B1 | 7/2003 | Roe et al. |
| 6,617,016 B2 | 9/2003 | Zhang et al. |
| 6,627,787 B1 | 9/2003 | Roe et al. |
| 6,692,196 B1 | 2/2004 | Simm et al. |
| 6,825,393 B2 | 11/2004 | Roe et al. |
| 6,861,571 B1 | 3/2005 | Roe et al. |
| 6,876,107 B2 | 4/2005 | Jacobs |
| 6,892,512 B2 | 5/2005 | Rice et al. |
| 6,899,036 B2 | 5/2005 | Lamb et al. |
| 6,925,784 B2 | 8/2005 | Escobar et al. |
| 6,928,789 B2 * | 8/2005 | Prakken .................. B65B 35/04 |
| | | 198/418.1 |
| 6,929,111 B2 | 8/2005 | Rovers |
| 6,970,769 B2 | 11/2005 | Rice et al. |
| 7,010,899 B2 | 3/2006 | McErlean et al. |
| 7,011,728 B2 | 3/2006 | Dewig et al. |
| 7,134,258 B2 | 11/2006 | Kalany et al. |
| 7,185,477 B2 | 3/2007 | Rice et al. |
| 7,204,192 B2 | 4/2007 | Lamb et al. |
| 7,248,938 B2 | 7/2007 | Scalfani et al. |
| 7,277,601 B2 | 10/2007 | Zorba et al. |
| 7,386,965 B2 | 6/2008 | McErlean et al. |
| 7,409,977 B2 | 8/2008 | Rice et al. |
| 7,412,814 B2 | 8/2008 | Rice et al. |
| 7,430,838 B2 | 10/2008 | Rice et al. |
| 7,478,749 B2 | 1/2009 | Clothier et al. |
| 7,515,984 B2 | 4/2009 | Scalfani et al. |
| 7,530,211 B2 | 5/2009 | McErlean et al. |
| 7,555,875 B2 | 7/2009 | Kim |
| 7,569,039 B2 | 8/2009 | Matsuda et al. |
| 7,584,589 B2 * | 9/2009 | Stafford, III .......... B65B 59/001 |
| | | 53/154 |
| 7,654,203 B2 | 2/2010 | Roop et al. |
| 7,668,618 B2 | 2/2010 | Szesko et al. |
| 7,684,652 B2 | 3/2010 | Zorab et al. |
| 7,761,180 B2 | 7/2010 | Scalfani et al. |
| 7,765,776 B1 | 8/2010 | Leu et al. |
| 7,770,364 B1 | 8/2010 | Leu et al. |
| 7,837,093 B1 | 11/2010 | Leu et al. |
| 7,837,107 B1 | 11/2010 | Leu et al. |
| 7,885,821 B2 | 2/2011 | Tait |
| 7,954,712 B2 | 6/2011 | Babcock et al. |
| 8,065,858 B2 | 11/2011 | Leu et al. |
| 8,087,579 B2 | 1/2012 | Leu et al. |
| 8,100,253 B2 | 1/2012 | Walsh |
| 8,109,066 B2 | 2/2012 | Leu et al. |
| 8,110,057 B2 | 2/2012 | Rice et al. |
| 8,117,809 B2 | 2/2012 | McErlean et al. |
| 8,136,332 B2 | 3/2012 | Rice et al. |
| 8,204,621 B2 | 6/2012 | Imai et al. |
| 8,275,481 B2 | 9/2012 | Rice et al. |
| 8,308,418 B2 | 11/2012 | Ma et al. |
| 8,322,613 B2 | 12/2012 | Leu et al. |
| 8,336,700 B2 | 12/2012 | Warecki et al. |
| 8,378,165 B2 * | 2/2013 | Visscher ............ A61F 13/55145 |
| | | 604/361 |
| 8,397,896 B2 | 3/2013 | Kleinikkink et al. |
| 8,453,821 B2 | 6/2013 | Hutter et al. |
| 8,474,603 B2 | 7/2013 | Warecki et al. |
| 8,480,834 B2 | 7/2013 | Rice et al. |
| 8,511,555 B2 | 8/2013 | Babcock et al. |
| 8,539,742 B2 | 9/2013 | McErlean et al. |
| 8,608,371 B2 | 12/2013 | Bartholomew et al. |
| 8,627,639 B2 | 1/2014 | Ali et al. |
| 8,657,729 B2 | 2/2014 | Yamamoto |
| 8,738,804 B2 | 5/2014 | Childress |
| 8,776,985 B2 | 7/2014 | Huettner et al. |
| 8,783,331 B2 | 7/2014 | Heinecke et al. |
| 8,789,678 B2 | 7/2014 | Kleinikkink et al. |
| 8,813,951 B2 | 8/2014 | Forsthoevel et al. |
| 8,827,071 B2 | 9/2014 | van de Loecht |
| 8,863,669 B2 * | 10/2014 | Young .................... H02P 6/006 |
| | | 104/292 |
| 8,966,864 B2 | 3/2015 | Rabec |
| 8,972,037 B2 | 3/2015 | Scalfani et al. |
| 9,045,183 B2 | 6/2015 | Laurence et al. |
| 9,046,890 B2 | 6/2015 | Krause et al. |
| 9,096,386 B2 | 8/2015 | Staunton et al. |
| 9,122,566 B2 | 9/2015 | Bastian, II et al. |
| 9,132,873 B1 | 9/2015 | Laurence et al. |
| 9,139,377 B2 | 9/2015 | Assante et al. |
| 9,204,920 B2 | 12/2015 | McPherson et al. |
| 9,221,482 B2 | 12/2015 | Gatterbauer et al. |
| 9,228,220 B2 | 1/2016 | Williams, Jr. |
| 9,228,221 B2 | 1/2016 | Williams, Jr. |
| 9,228,222 B2 | 1/2016 | Williams, Jr. |
| 9,233,800 B2 | 1/2016 | Senn et al. |

(56) References Cited

U.S. PATENT DOCUMENTS

| | | | |
|---|---|---|---|
| 9,260,741 B2 | 2/2016 | Williams, Jr. | |
| 9,266,706 B2 | 2/2016 | Forestelli et al. | |
| 9,274,529 B2 | 3/2016 | Ben-shachar | |
| 9,315,334 B2 | 4/2016 | Mellars et al. | |
| 9,382,101 B2 | 7/2016 | Friedrich | |
| 9,387,882 B2 | 7/2016 | Han | |
| 9,415,441 B2 | 8/2016 | Heinecke | |
| 9,457,856 B2 | 10/2016 | Yao et al. | |
| 9,459,273 B2 | 10/2016 | Moix et al. | |
| 9,470,702 B2 | 10/2016 | Pollack | |
| 9,511,681 B2 | 12/2016 | Wemersbach et al. | |
| 9,540,190 B2 | 1/2017 | Jochim et al. | |
| 9,592,925 B2 | 3/2017 | Leu et al. | |
| 9,611,107 B2 | 4/2017 | Wemersbach et al. | |
| 9,643,794 B2 | 5/2017 | Wipf et al. | |
| 9,656,766 B2 | 5/2017 | Friedrich | |
| 9,658,239 B2 | 5/2017 | Eberhardt et al. | |
| 9,659,801 B2 | 5/2017 | Ma et al. | |
| 9,671,418 B2 | 6/2017 | Mellars et al. | |
| 2003/0136086 A1* | 7/2003 | Kalany | B65G 54/02 53/443 |
| 2003/0233082 A1 | 12/2003 | Kline et al. | |
| 2004/0102748 A1 | 5/2004 | Hirotsu | |
| 2005/0107764 A1 | 5/2005 | Matsuda et al. | |
| 2007/0058840 A1 | 3/2007 | Singh et al. | |
| 2008/0216451 A1* | 9/2008 | Stafford | B65B 35/54 53/445 |
| 2012/0061015 A1 | 3/2012 | LaVon et al. | |
| 2012/0061016 A1 | 3/2012 | LaVon et al. | |
| 2013/0072887 A1 | 3/2013 | LaVon et al. | |
| 2013/0084259 A1 | 4/2013 | Lee | |
| 2013/0130879 A1 | 5/2013 | Schoon et al. | |
| 2013/0211356 A1 | 8/2013 | Nishikawa et al. | |
| 2013/0255861 A1 | 10/2013 | Schneider | |
| 2013/0255862 A1 | 10/2013 | Schneider et al. | |
| 2013/0255863 A1 | 10/2013 | LaVon et al. | |
| 2013/0255864 A1 | 10/2013 | Schneider et al. | |
| 2013/0255865 A1 | 10/2013 | Brown et al. | |
| 2013/0306226 A1 | 11/2013 | Zink et al. | |
| 2014/0157732 A1 | 6/2014 | Gasber | |
| 2014/0170085 A1 | 6/2014 | Peters | |
| 2014/0338287 A1* | 11/2014 | Pelagatti | B65B 35/50 53/202 |
| 2015/0078876 A1 | 3/2015 | Michler et al. | |
| 2015/0158611 A1 | 6/2015 | Kalany et al. | |
| 2015/0203231 A1 | 7/2015 | Brandhorst et al. | |
| 2015/0225100 A1* | 8/2015 | Jelken | B65B 5/067 53/443 |
| 2015/0273691 A1 | 10/2015 | Pollack | |
| 2015/0276774 A1* | 10/2015 | Pollack | G01N 35/02 414/749.1 |
| 2016/0038217 A1 | 2/2016 | McPherson et al. | |
| 2016/0086118 A1 | 3/2016 | Reed et al. | |
| 2016/0114988 A1 | 4/2016 | Unterseher | |
| 2016/0161358 A1 | 6/2016 | Williams, Jr. | |
| 2016/0207658 A1* | 7/2016 | Bellante | B65B 51/02 |
| 2016/0244271 A1 | 8/2016 | Walter et al. | |
| 2016/0280410 A1 | 9/2016 | Mann et al. | |
| 2017/0065462 A1 | 3/2017 | Arnold | |
| 2018/0072445 A1 | 3/2018 | Burkhard et al. | |
| 2018/0072551 A1 | 3/2018 | Burkhard et al. | |
| 2018/0072552 A1 | 3/2018 | Orndorff et al. | |
| 2018/0074477 A1 | 3/2018 | Burkhard et al. | |
| 2018/0074478 A1 | 3/2018 | Burkhard et al. | |
| 2018/0076069 A1* | 3/2018 | Burkhard | B65B 59/003 |

FOREIGN PATENT DOCUMENTS

| | | |
|---|---|---|
| EP | 1645340 B1 | 10/2010 |
| EP | 2500296 B1 | 2/2012 |
| EP | 2746165 A1 | 6/2014 |
| EP | 2889238 A1 | 7/2015 |
| EP | 2915521 A1 | 9/2015 |
| EP | 2998232 A1 | 3/2016 |
| EP | 3002222 B1 | 4/2017 |
| JP | H 01271312 A1 | 10/1989 |
| WO | WO 9627544 A1 | 9/1996 |
| WO | WO 9959738 | 11/1999 |
| WO | WO 200185581 | 11/2001 |
| WO | WO 200308113 | 1/2003 |
| WO | WO 201611464 | 1/2016 |
| WO | WO 2017221317 A1 | 12/2017 |

\* cited by examiner

METHOD AND APPARATUS FOR FLEXIBLY ASSEMBLING PACKAGES OF ABSORBENT ARTICLES

FIELD OF THE INVENTION

The present disclosure relates to methods for manufacturing absorbent articles, and more particularly, to apparatuses and methods for making packages of one or more absorbent articles.

BACKGROUND OF THE INVENTION

Along an assembly line, various types of disposable absorbent articles, such as diapers, sanitary napkins, and pant liners, may be assembled by adding components to and otherwise modifying advancing, continuous webs of material. Webs of material and component parts used to manufacture diapers may include: backsheets, topsheets, absorbent cores, front and/or back ears, fastener components, and various types of elastic webs and components such as leg elastics, barrier leg cuff elastics, and waist elastics. Webs of material and component parts used to manufacture sanitary napkins and/or panty liners may include: backsheets, topsheets, secondary topsheets, absorbent core components, release paper wrappers, and the like. Once the desired component parts are assembled, the advancing web(s) and component parts are subjected to a final knife cut to separate the web(s) into discrete absorbent articles. The absorbent articles may also sometimes be folded and/or individually wrapped.

The assembled absorbent articles may be advanced from assembly lines to packaging apparatuses that are configured to place the absorbent articles in packages. To help maintain relatively low manufacturing costs, absorbent article assembly lines may be configured to operate at relatively high speeds to produce relatively large quantities of identical absorbent articles as quickly as possible. In addition, dedicated packaging apparatuses that receive absorbent articles from assembly lines may be specifically configured to place predetermined quantities of such identical absorbent articles together in packages.

In some instances, it may be desirable for some suppliers and/or manufactures to provide packages containing various quantities and/or types of absorbent articles for various purposes. For example, a supplier may have a need to provide packages containing relatively low quantities of absorbent articles for various purposes. Such "low count" packages may be sent to a relatively small group of consumers for test marketing purposes. In another example, a supplier may have a need to provide packages containing different absorbent articles. Such "variety" packages may include absorbent articles having different absorbent capacities, sizes, and/or different aesthetic characteristics.

However, utilizing established assembly lines and packaging apparatuses to create small count and/or variety packages of absorbent articles may present certain challenges, because assembly lines and packaging apparatuses may be configured to operate at high speeds and to produce packages containing predetermined quantities of identical absorbent articles. For example, an entire assembly line may need to be temporarily stopped in order to reconfigure the assembly line and/or packaging apparatus to enable assembly of the desired packaging arrangements. In some examples, the assembly line and/or packaging apparatus may also be operated at relatively slow speeds while assembling such desired packaging arrangements. Consequently, it may be cost prohibitive and/or inefficient to reconfigure and/or operate assembly lines and associated packing machines configured for mass production for the purposes of producing relatively low quantities of specialized packages. In some instances, suppliers may utilize manual labor to produce such packages by hand, but such operations can be cost prohibitive, slow, and inefficient.

Consequently, it may be beneficial to provide flexible methods and apparatuses that utilize high speed absorbent article assembly lines to produce various assortments of packages of absorbent articles, such as low count and/or variety packages, without having to stop and/or reconfigure dedicated assembly and packaging processes or rely on manual packaging to make such packages.

SUMMARY OF THE INVENTION

In one form, a method for producing a package of one or more absorbent articles comprises: providing a carrier movably connected with a track; assembling absorbent articles with an assembly line; advancing the absorbent articles from the assembly line along a first path toward a first packaging apparatus; diverting an absorbent article from the first path to a second path; advancing the diverted absorbent article along the second path; transferring the diverted absorbent article from the second path to the carrier in a receiving zone; moving the carrier along the track with a linear synchronous motor from the receiving zone to a drop off zone; and transferring the diverted absorbent article from the carrier in the drop off zone to a second packaging apparatus.

In another form, a method for producing a package of absorbent articles comprises: providing a first carrier and a second carrier movably connected with a track, wherein the first and second carriers are independently driven along the track with a linear synchronous motor; assembling first absorbent articles with a first assembly line and assembling second absorbent articles with a second assembly line; advancing the first absorbent articles from the first assembly line along a first path toward a first packaging apparatus; advancing the second absorbent articles from the second assembly line along a second path toward a second packaging apparatus; diverting a first absorbent article from the first path to the first carrier in a first receiving zone; diverting a second absorbent article from the second path to the second carrier in a second receiving zone; moving the first carrier with the diverted first absorbent article along the track with the linear synchronous motor from the first receiving zone to a drop off zone; moving the second carrier with the diverted second absorbent article along the track with the linear synchronous motor from the second receiving zone to the drop off zone; transferring the diverted first absorbent article from the first carrier and the diverted second absorbent article from the second carrier in the drop off zone to a third packaging apparatus to place the diverted first absorbent article and the diverted second absorbent article together in a package.

In yet another form, a method for producing a package of absorbent articles comprises: providing a carrier movably connected with a track; assembling first absorbent articles with a first assembly line and assembling second absorbent articles with a second assembly line; advancing the first absorbent articles from the first assembly line along a first path toward a first packaging apparatus; advancing the second absorbent articles from the second assembly line along a second path toward a second packaging apparatus; diverting a first absorbent article from the first path; transferring the diverted first absorbent article from the first path to the carrier in a first receiving zone; moving the carrier and the diverted first absorbent article along the track with a linear synchronous motor from the first receiving zone to a second receiving zone; diverting a second absorbent article from the second path; transferring the diverted second absorbent article from the second path to the carrier in the second receiving zone; moving the carrier with the diverted first and second absorbent articles along the track with the linear synchronous motor from the second receiving zone to a drop off zone; and transferring the diverted first absorbent article and the diverted second absorbent article from the carrier in the drop off zone to a third packaging apparatus to place the diverted first absorbent article and the diverted second absorbent article together in a package.

DETAILED DESCRIPTION OF THE INVENTION

Figure 1:
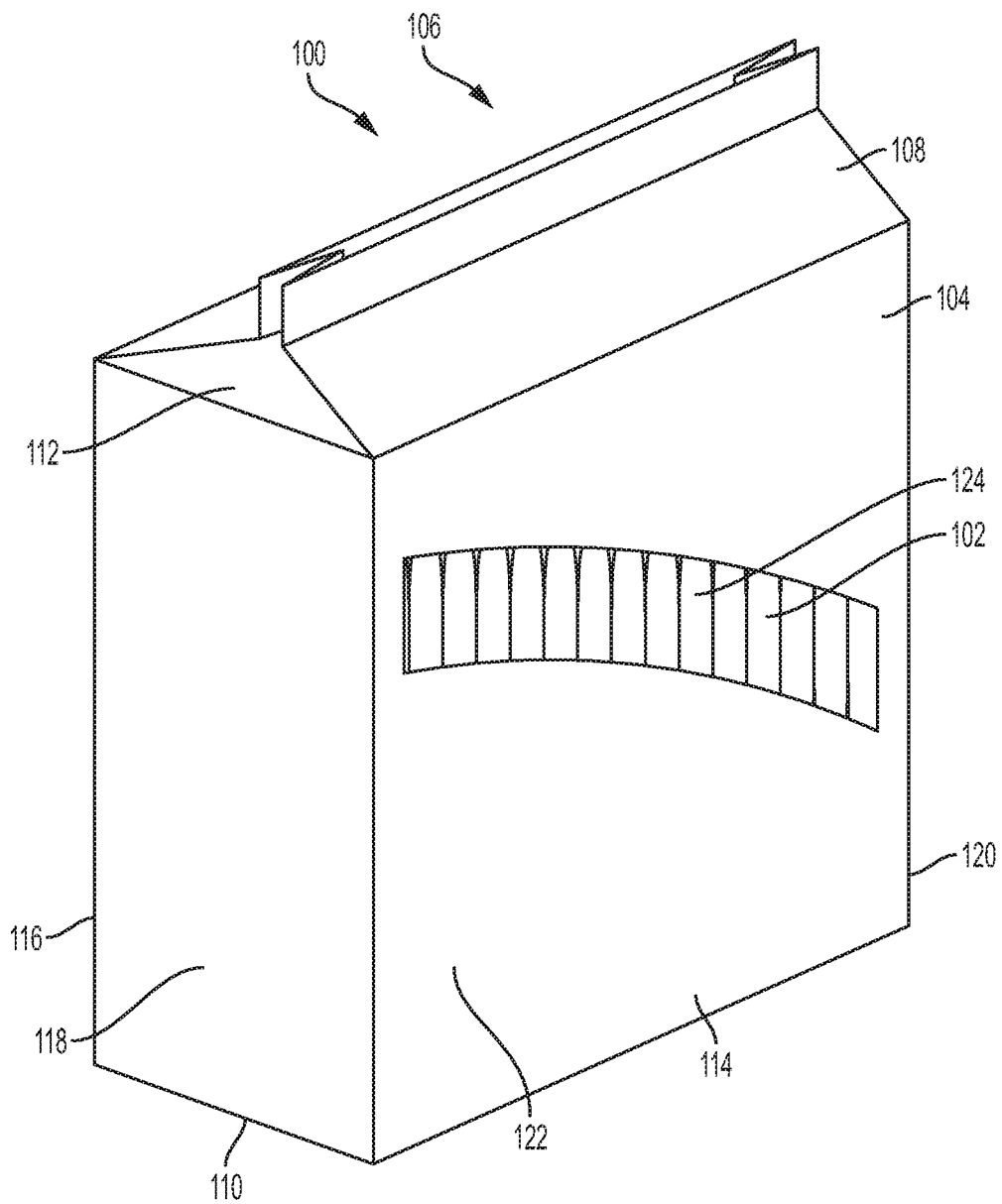
FIG. 1 is a perspective view of a package of absorbent articles.

"Absorbent article" is used herein to refer to consumer products whose primary function is to absorb and retain soils and wastes. Absorbent articles can comprise sanitary napkins, tampons, panty liners, interlabial devices, wound dressings, wipes, disposable diapers including taped diapers and diaper pants, inserts for diapers with a reusable outer cover, adult incontinent diapers, adult incontinent pads, and adult incontinent pants. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "substrate" is used herein to describe a material which is primarily two-dimensional (i.e. in an XY plane) and whose thickness (in a Z direction) is relatively small (i.e. $\frac{1}{10}$ or less) in comparison to its length (in an X direction) and width (in a Y direction). Non-limiting examples of substrates include a web, layer or layers or fibrous materials, nonwovens, films and foils such as polymeric films or metallic foils. These materials may be used alone or may comprise two or more layers laminated together. As such, a web is a substrate.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

The term "taped diaper" (also referred to as "open diaper") refers to disposable absorbent articles having an initial front waist region and an initial back waist region that are not fastened, pre-fastened, or connected to each other as packaged, prior to being applied to the wearer. A taped diaper may be folded about the lateral centerline with the interior of one waist region in surface to surface contact with the interior of the opposing waist region without fastening or joining the waist regions together. Example taped diapers are disclosed in various suitable configurations U.S. Pat. Nos. 5,167,897, 5,360,420, 5,599,335, 5,643,588, 5,674,216, 5,702,551, 5,968,025, 6,107,537, 6,118,041, 6,153,209, 6,410,129, 6,426,444, 6,586,652, 6,627,787, 6,617,016, 6,825,393, and 6,861,571; and U.S. Patent Publication Nos. 2013/0072887 A1; 2013/0211356 A1; and 2013/0306226 A1, all of which are incorporated by reference herein.

The term "pant" (also referred to as "training pant", "pre-closed diaper", "diaper pant", "pant diaper", and "pull-on diaper") refers to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer. A pant can be preformed or pre-fastened by various techniques including, but not limited to, joining together portions of the article using any refastenable and/or permanent closure member (e.g., seams, heat bonds, pressure welds, adhesives, cohesive bonds, mechanical fasteners, etc.). A pant can be preformed anywhere along the circumference of the article in the waist region (e.g., side fastened or seamed, front waist fastened or seamed, rear waist fastened or seamed). Example diaper pants in various configurations are disclosed in U.S. Pat. Nos. 4,940,464; 5,092,861; 5,246,433; 5,569,234; 5,897, 545; 5,957,908; 6,120,487; 6,120,489; 7,569,039 and U.S. Patent Publication Nos. 2003/0233082 A1; 2005/0107764 A1, 2012/0061016 A1, 2012/0061015 A1; 2013/0255861 A1; 2013/0255862 A1; 2013/0255863 A1; 2013/0255864 A1; and 2013/0255865 A1, all of which are incorporated by reference herein.

The term "feminine hygiene articles" refers to disposable absorbent articles used by women for catamenial protection. Such feminine hygiene articles may include sanitary napkins, tampons, interlabial products, incontinence devices, and pantiliners. Non-limiting examples of panty liners and sanitary napkins include those disclosed in U.S. Pat. Nos. 4,324,246; 4,463,045; 4,342,314; 4,556,146; 4,589,876; 4,687,478; 4,950,264; 5,009,653; 5,267,992; and 6,004,893.

The term "different types of absorbent articles" refers to absorbent articles which include at least one of the absorbent articles having a different physical property or structure from that of at least another one of the absorbent articles. Examples of a physical property or a structure may include absorbent capacity; aesthetic appearance, such as for example, color and/or graphics; dimension(s), such as for example, longitudinal length, traversal width, and/or thickness, of absorbent articles; types or kinds of absorbent articles, such as for example, sanitary napkins, tampons, panty liners, interlabial devices, wound dressings, wipes, disposable diapers including taped diapers and diaper pants, inserts for diapers with a reusable outer cover, adult incontinent diapers, adult incontinent pads, and adult incontinent pants, and combinations thereof.

The term "graphic" refers to printed areas of substrates. Graphics may include a color difference or transition of one or more colors and may define images or designs that are constituted by a figure (for example, a line(s)), a symbol or character), or the like. A graphic may include an aesthetic image or design that can provide certain benefit(s) when viewed. A graphic may be in the form of a photographic image. A graphic may also be in the form of a 1-dimensional (1-D) or 2-dimensional (2-D) bar code or a quick response (QR) bar code. A graphic design is determined by, for example, the color(s) used in the graphic (individual pure ink or spot colors as well as built process colors), the sizes of the entire graphic (or components of the graphic), the positions of the graphic (or components of the graphic), the movements of the graphic (or components of the graphic), the geometrical shapes of the graphic (or components of the graphics), the number of colors in the graphic, the variations of the color combinations in the graphic, the number of graphics printed, the disappearance of color(s) in the graphic, and the contents of text messages in the graphic.

Graphics may be configured to be different graphics, standard graphics, custom graphics, and/or personalized graphics. "Different in terms of graphic design" means that graphics are intended to be different when viewed by users or consumers with normal attentions. Thus, two graphics having a graphic difference(s) which are unintentionally caused due to a problem(s) or an error(s) in a manufacture process, for example, are not different from each other in terms of graphic design. "Standard" or "standardized" refers to graphics, products, and/or articles that have the same aesthetic appearance without intending to be different from each other. The term "custom" or "customized" refers to graphics, products, and/or articles that are changed to suit a small demographic, region, purchaser, customer, or the like. Custom graphics may be selected from a set of graphics. For example, custom graphics may include animal depictions selected from groups of animals, such as farm animals, sea creatures, birds, and the like. In other examples, custom graphics may include nursery rhymes and the like. In one scenario, custom products or articles may be created by a purchaser of such products or articles wherein the purchaser selects graphics for the articles or products from a set of graphics offered by a manufacturer of such articles or products. Custom graphics may also include "personalized" graphics, which may be graphics created for a particular purchaser. For example, personalized graphics may include a person's name alone or in combination with a design.

The present disclosure relates to methods for making packages of one or more absorbent articles, and more particularly, to apparatuses and methods configured to utilize existing high speed assembly lines with dedicated packaging apparatuses to assemble various kinds of packages of absorbent articles. The methods and apparatuses herein are configured to divert absorbent articles advancing from an assembly line before reaching a dedicated packaging apparatus. The diverted absorbent articles are transported to a selectable packaging apparatus to be placed in containers containing desired quantities and/or types of absorbent articles. The containers of diverted absorbent articles may be referred to herein as "select packages" and may comprise different types of absorbent articles and/or may comprise absorbent articles having different features such as: graphics, perfume scents, odor neutralizers, lotions, material constructions, sizes, lengths, widths, thicknesses, and/or absorbent capacities. As discussed in more detail below, the methods and apparatuses herein may be configured with one or more carriers movably connected with a track, wherein a linear synchronous motor may be used to independently move the carriers along the track. Diverted absorbent articles mentioned above are transferred to a carrier in a receiving zone. The carrier and diverted absorbent articles are moved along the track with the linear synchronous motor from the receiving zone to a drop off zone. The diverted absorbent articles are then transferred from the carrier in the drop off zone to a selectable packaging apparatus, which may place the diverted absorbent articles into a container to create a select package. As such, the methods and apparatuses provide the ability to flexibly produce various assortments of select packages of absorbent articles, such as low count and/or variety packages, without having to stop and/or reconfigure absorbent article assembly lines and/or associated dedicated packaging apparatuses.

As previously mentioned, the processes and apparatuses discussed herein may be used to assemble various select packages of different types of absorbent articles. It is to be appreciated that such select packages may contain one or more absorbent articles, such as disclosed for example in U.S. Pat. Nos. 5,897,542; 6,318,555; and 6,454,095; and U.S. Patent Publication No. 2004/0102748 A1. To help provide additional context to the subsequent discussion of the process embodiments, the following provides a general description of packages of absorbent articles that may be produced with the methods and apparatuses disclosed herein.

FIG. 1 shows a simplified perspective illustration of a package 100 that may include one or more absorbent articles 102 positioned inside a container 104. It is to be appreciated that the package 100 may be configured as a select package 106 that may be assembled in accordance with the apparatuses and methods disclosed herein. The container 104 may be formed from various types of material and may be configured in various shapes and sizes. For example, the container 104 may be configured as a carton which is formed from a cardboard material. In some examples, the container may be configured as a flexible bag which is formed from a film material. Such a film material may be made of paper, plastic, and/or various types of recyclable material, and may also comprise a laminate structure of two or more materials. The film material may also comprise polymeric films, polypropylene films, and/or polyethylene films. As shown in FIG. 1, the container 104 may include a top side 108 and a bottom side 110 that may be closed by forming gussets 112. The container may also include a front panel 114 and a rear panel 116, wherein the front and rear panels 114, 116 are connected with and separated by opposing first and second side panels 118, 120. The front panel 114, the rear panel 116, the first side panel 118, and/or the second side panel 120 may be substantially planar as shown in FIG. 1 and may also define an outer surface 122 of the container 104.

With continued reference to FIG. 1, the container 104 may also include one or more windows 124, wherein absorbent articles 102 housed inside the container 104 may be seen through the window 124. It is to be appreciated that the absorbent articles 102 may be configured in various ways. For example, one or more the absorbent articles 102 may include an individual flexible wrapper or bag that wraps or contains a respective absorbent article 102. In some configurations, one or more of the absorbent articles 102 may be placed and stored in the container 104 without being individually wrapped or contained by a flexible wrapper or bag. It is also to be appreciated that one or more of the absorbent articles 102 may be folded before being placed and stored in the container 104, such as disclosed for example in U.S. Pat. Nos. 5,569,228; 6,074,376; 8,657,729 U.S. Patent Publication Nos. 2007/0058840 A1; 2013/0130879 A1; and 2017/0065462 A1. In some configurations, the absorbent articles 102 may be stacked to form one or more stacks in the container 104.

Figure 2A:
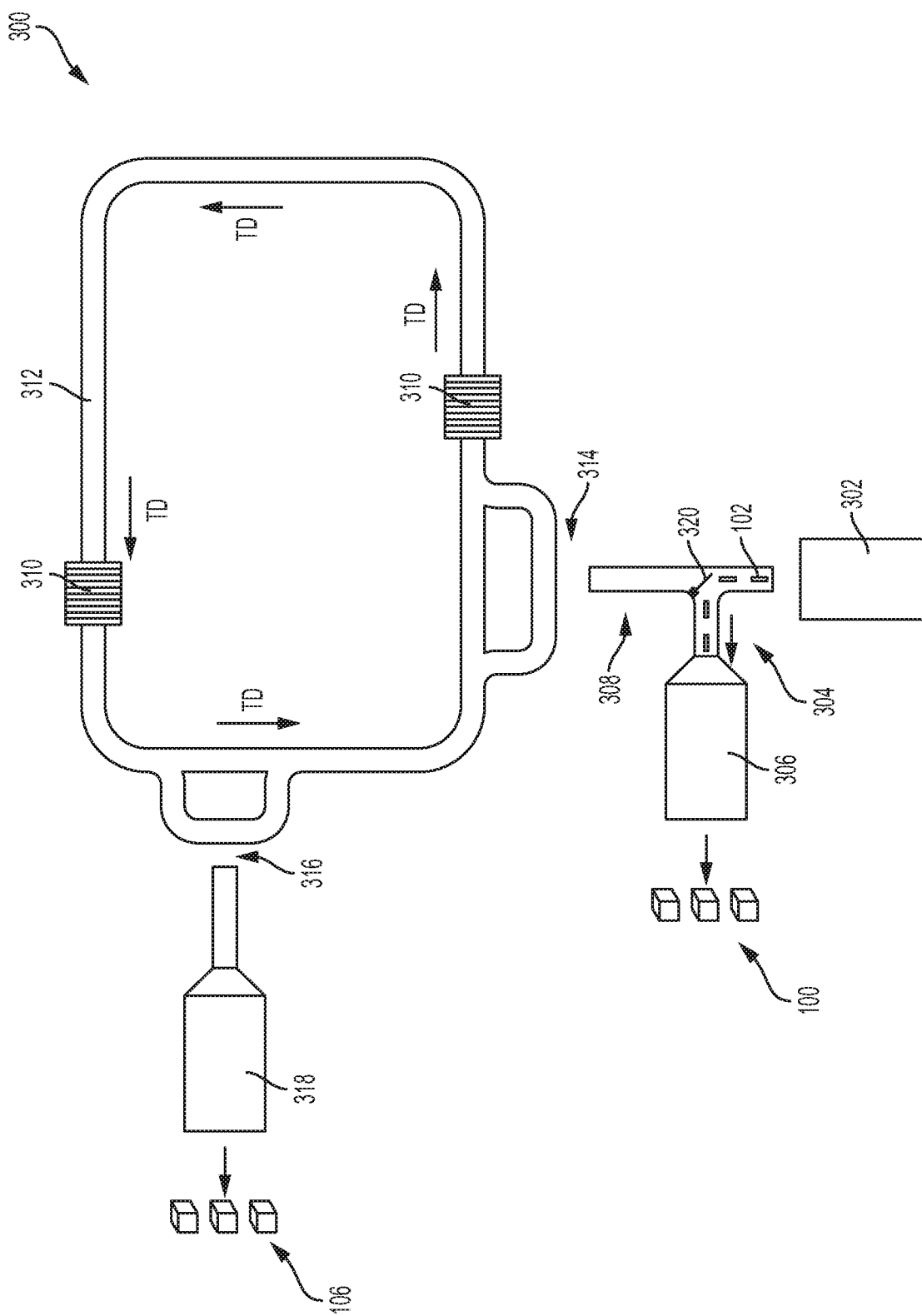
FIG. 2A is a schematic view of an apparatus adapted to assemble packages of absorbent articles in a first mode of operation.
Figure 2B:
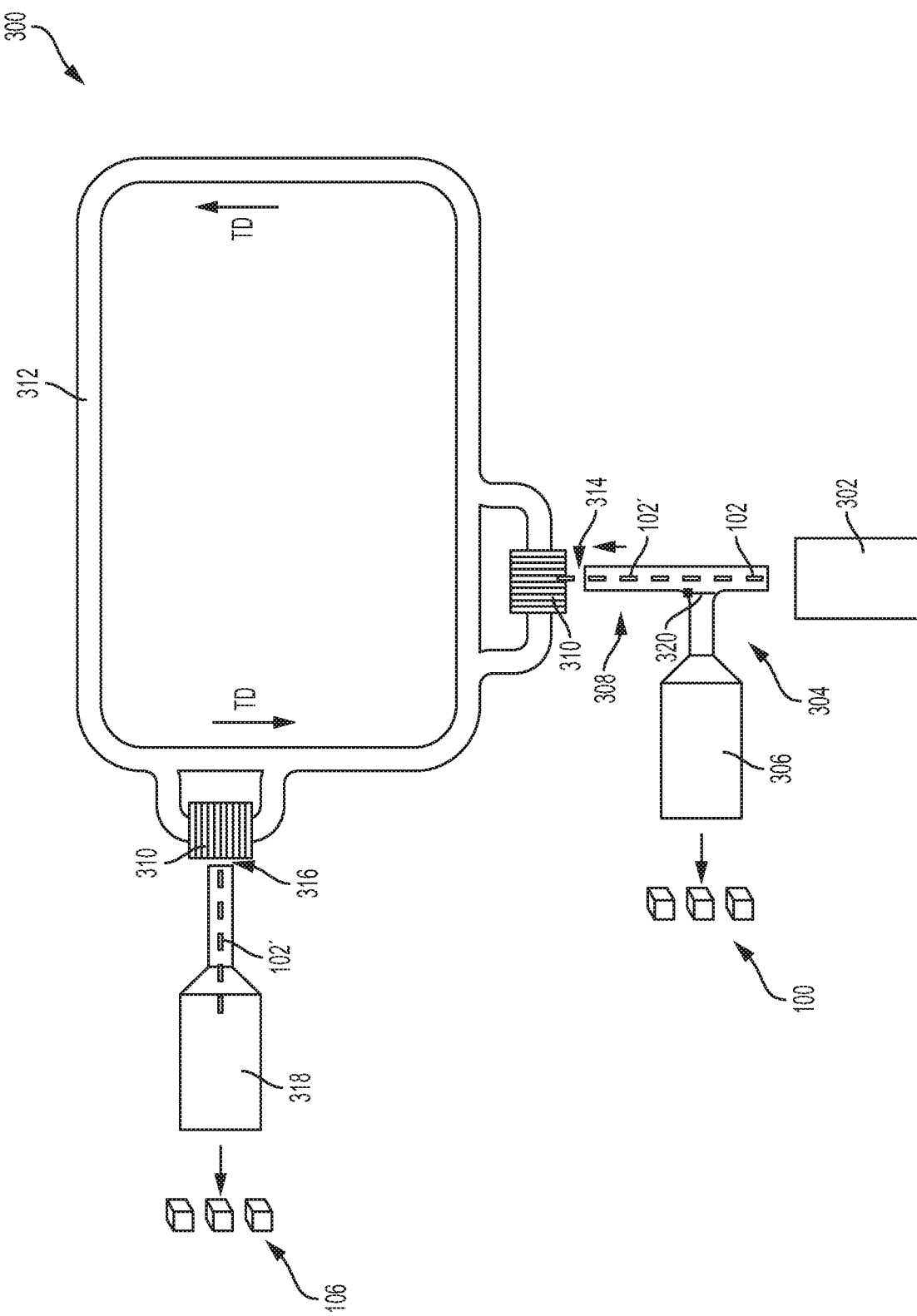
FIG. 2B is a schematic view of an apparatus adapted to assemble packages of absorbent articles operating in a second mode of operation.

As previously mentioned, apparatuses and methods according to the present disclosure may be utilized to produce select packages 106 of absorbent articles 102. For example, FIGS. 2A and 2B show schematics view of an apparatus 300 adapted to assemble select packages 106 of absorbent articles 102. The apparatus 300 shown in FIGS. 2A and 2B operates in conjunction with an assembly line 302 configured to manufacture absorbent articles 102. In a first mode of operation shown in FIG. 2A, the absorbent articles 102 may advance from the assembly line 302 along a first path 304 toward a first packaging apparatus 306. As discussed above, the assembly line 302 may be configured to assemble absorbent articles 102 at relatively high speeds, wherein the first packaging apparatus 306 may be configured to receive and place predetermined quantities of assembled absorbent articles 102 into containers 104 as part of a mass production process to produce packages 100 of absorbent articles 102.

In a second mode of operation shown in FIG. 2B, one or more of the absorbent articles 102 advancing from the assembly line 302 may be diverted from the first path 304 to a second path 308. The diverted absorbent articles 102' may then advance along the second path 308 and transferred to a carrier 310. The carrier 310 may be movably connected with a track 312. In operation, the carrier 310 may be moved along the track 312 to a receiving zone 314 where diverted absorbent articles 102' may be transferred to the carrier 310. The carrier 310 may then be moved to a drop off zone 316 where diverted absorbent may be transferred from the carrier 310 to a selective packaging apparatus 318. The selective packing apparatus then places the diverted absorbent articles 102' into containers 104 to create select packages 106 of absorbent articles 102.

It is to be appreciated that the first path 304 and/or the second path 308 may configured in various ways to advance absorbent articles 102 from the assembly line 302. For example, the first path 304 and/or the second path 308 may comprise one or conveyor belts. In addition, various types of diverter mechanisms 320 may be used to divert absorbent articles from the first path 304 to the second path 308, such as for example, a pivot plate. Example of various types of conveyor arrangements and diverter mechanisms 320 are available from Optima Machinery Corporation, D. Cloostermans N V, and Krones A G. It is also to be appreciated that the assembly lines herein may be configured without a first packaging apparatus 306. As such, the apparatuses 300 herein may be configured to transport absorbent articles 102 directly from such assembly lines to one or more selective packaging apparatuses 318 without having to divert the absorbent articles from a first path 304 to a second path 308.

Figure 3A:
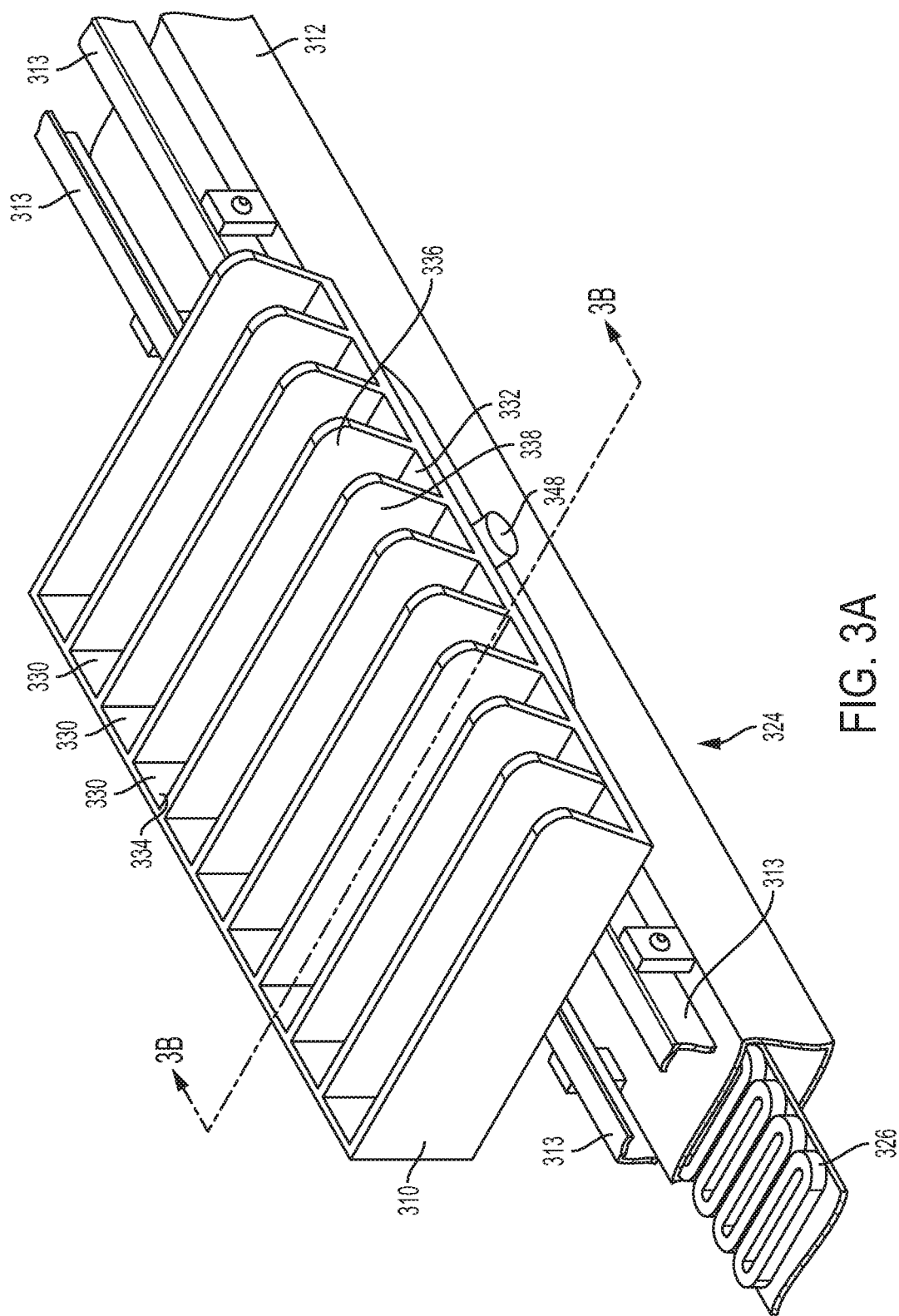
FIG. 3A is a detailed view of a carrier and track.
Figure 3B:
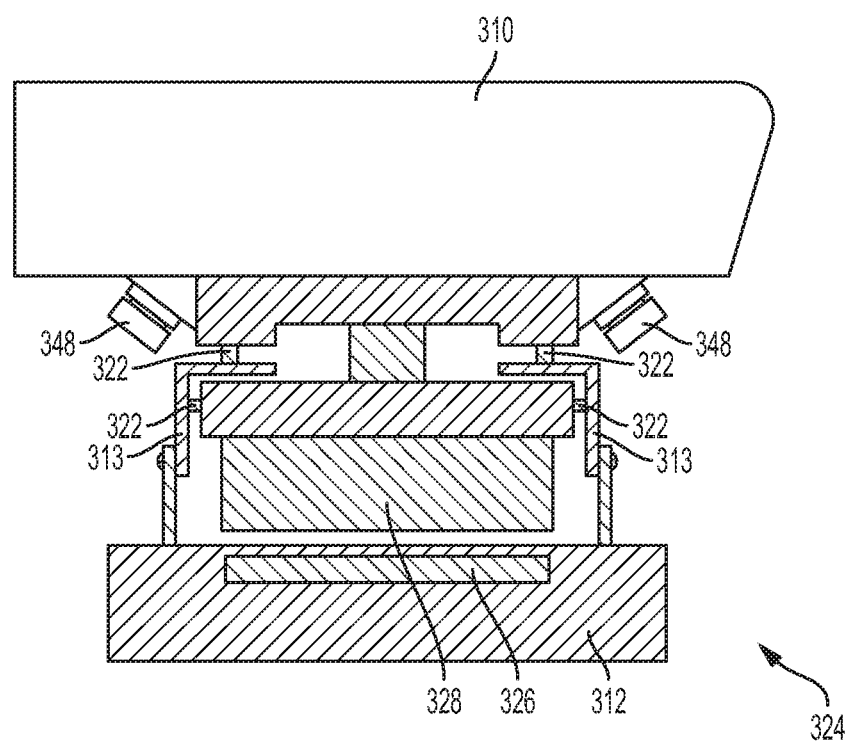
FIG. 3B is a sectional view of the carrier and track taken along line 3B-3B of FIG. 3A.

As previously mentioned, the apparatus 300 may include one or more carriers 310 movably connected with a track 312. FIGS. 3A and 3B show details of an example carrier 310 and track 312 arrangement. The track may include rails 313 and the carrier 310 may include wheels 322 adapted to roll along the rails 313. In addition, the apparatus 300 may include a linear synchronous motor 324 to move the carriers 310 independently of each other along the track 312 between receiving zones 314 and drop off zones 316. As shown in FIGS. 3A and 3B, the linear synchronous motor 324 may include conductive propulsion coils 326 connected with the track 312 and a permanent magnet 328 connected with the carrier 310. A power source can be used to energize of the conductive propulsion coils 326 that interact with the permanent magnet 328 to propel the carriers along the track 312 with electromagnetic forces. A control system may be used to control the energization of the conductive propulsion coils 326 to control the propulsion of the carriers 310 along the track 312. It is to be appreciated that various types of carriers 310, tracks 312, controllers, and/or linear synchronous motor 324 arrangements may be used, such as disclosed for example in U.S. Pat. Nos. 3,803,466; 7,134,258; 8,100,253; 9,511,681; and 9,611,107 and U.S. Patent Publication Nos. 2018/0072445 A1; 2018/0072551 A1; 2018/0072552 A1; 2018/0076069 A1; 2018/0074478 A1; and 2018/0074477 A1, as well as related components available from MagneMotion of Devens, Mass., U.S.A.

Figure 3C:
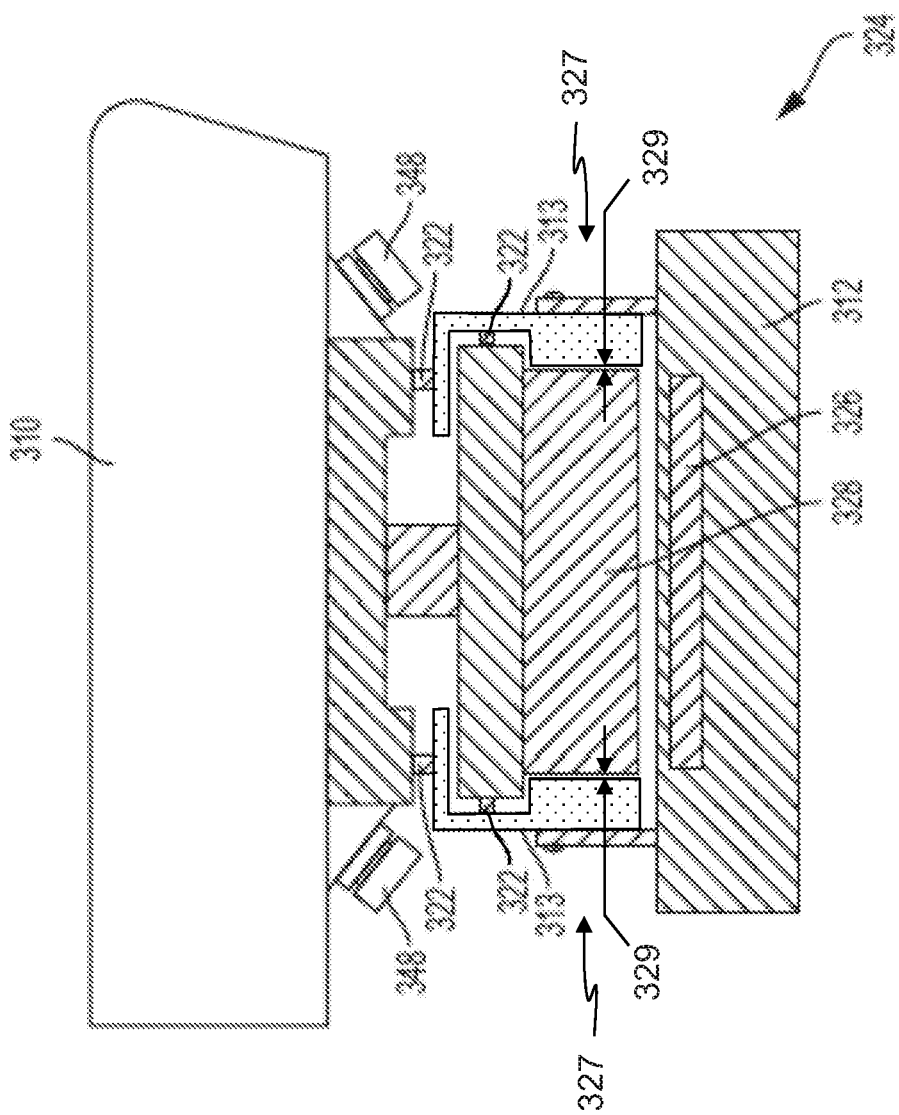
FIG. 3C is a sectional view of the carrier and track of FIG. 3B configured with an eddy current brake.

In some configurations, the track 312 may be arranged in a horizontal orientation, wherein the entire track is arranged with a constant elevation. In some configurations, the track 312 may be arranged with varying elevations, wherein portions of the track 312 have inclined and/or declined regions, also referred to herein as sloped regions. In situations when power may be removed from the conductive propulsion coils 326 while a carrier 310 is positioned on a sloped region of the track 312, gravitational forces may cause the carrier 310 to uncontrollably accelerate down the sloped region of the track 312. Such uncontrolled acceleration of the carrier 310 may be undesired and may create unsafe conditions for personnel and/or equipment. As such, the carrier 310 may be configured with a brake to slow and/or stop the carrier from accelerating down a sloped region of track 312. For example, as shown in FIG. 3C, the track 312 may be configured to interact with the moving carrier 310 to create an eddy current brake 327. As shown in FIG. 3C, the rails 313 of the track 312 in sloped regions may be configured to define relatively small air gaps 329 between the permanent magnet 328 and the rails 313. The rails may be made of a non-ferromagnetic conductive metal, such as aluminum or copper. In turn, as a carrier 310 begins to move down a sloped region of the track 312, the permanent magnet 328 induces eddy currents in the rails 313, which oppose the direction of travel of the carrier 310. The higher the velocity of the carrier 310, the stronger the eddy current effect that counteracts the movement of the carrier 310. And the smaller the air gap 329, the stronger the eddy current effect that counteracts the movement of the carrier 310.

Thus, the carrier 310 may move down the sloped region of the track 312, and the carrier's peak velocity may be limited by the eddy current braking effect from the rails 313. When power is removed from the conductive propulsion coils 326, the eddy current braking effect may cause the carrier 310 to coast down the sloped region of the track 312 relatively slowly and then stop at the bottom of the sloped region, helping to mitigate unsafe conditions for the equipment or personnel.

Figure 4A:
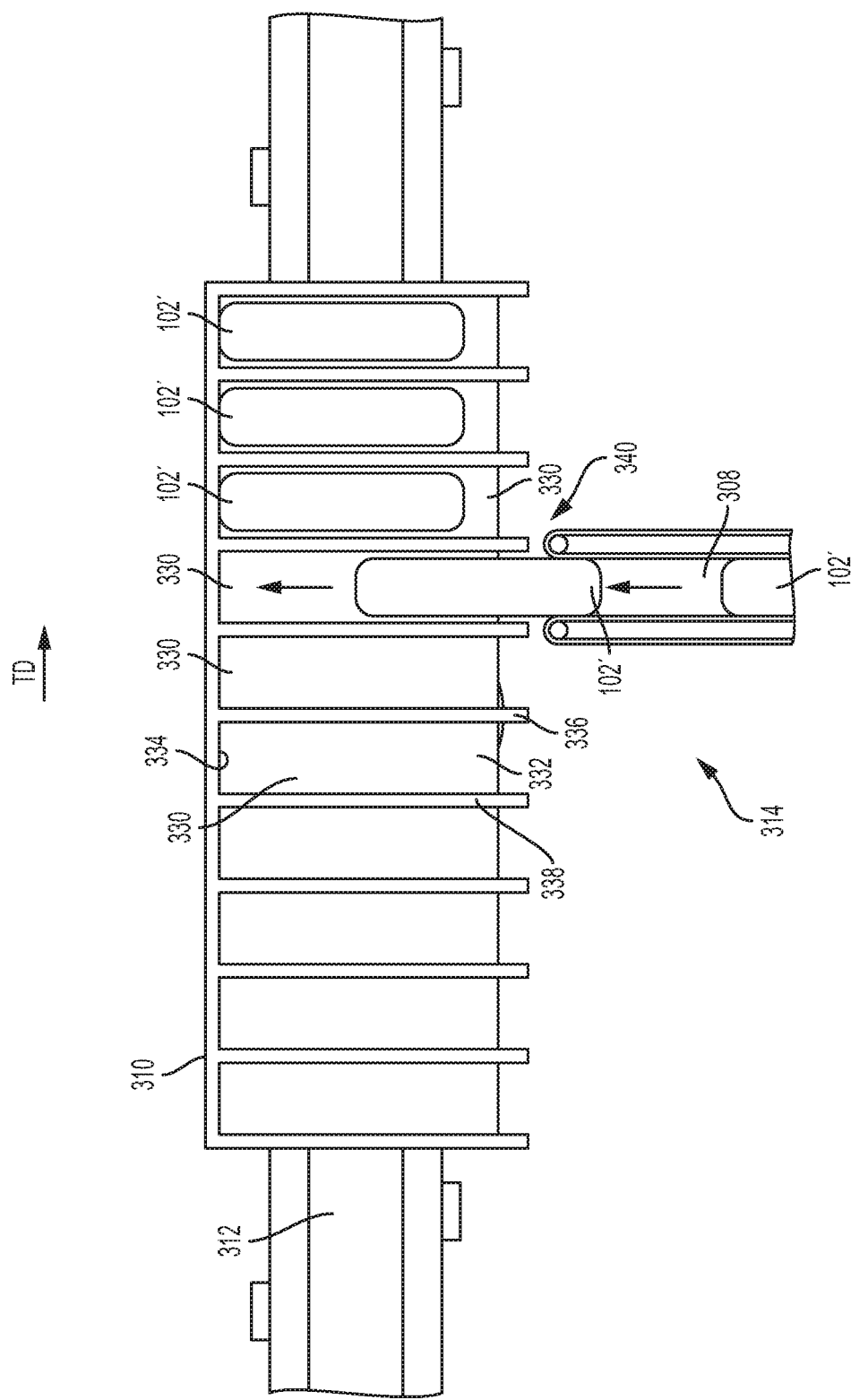
FIG. 4A is a detailed top schematic view of a carrier advancing through a receiving zone.

It is to be appreciated that the carrier 310 may be configured in various ways to hold and transport diverted absorbent articles 102' between receiving zones 314 and drop off zones 316. For example, the carrier 310 in FIGS. 3A and 4A, includes a plurality of receptacles 330, wherein each receptacle 330 may be adapted to receive a diverted absorbent article 102' advancing from the second path 308 and the assembly line 302. Each receptacle 330 may be defined by a bottom wall 332, a rear wall 334, a first side wall 336, and a second side wall 338 spaced apart from the first side wall 336, wherein the first side wall 336 and the second side wall 338 may be both connected with the rear wall 334. Once a diverted absorbent article 102' is inserted into a receptacle 330, the carrier 310 is advanced in a transport direction TD. In some configurations, the carrier 310 and the diverted absorbent article 102' may advance from the receiving zone 314 without receiving additional diverted absorbent articles 102'. In some configurations, once an empty receptacle 330 receives a diverted absorbent article 102', the receptacle 330 and the diverted absorbent article 102' are advanced in the transport direction TD to position an adjacent empty receptacle 330 at a discharge or downstream end 340 of the second path 308 to receive a subsequently advancing diverted absorbent article 102'. The sequence may be repeated to fill a plurality of receptacles 330 with diverted absorbent articles 102'. Once the desired number of diverted absorbent articles 102' have been received in receptacles 330, the carrier 310 may be advanced in the transport direction TD from the receiving zone 314. As shown in FIG. 2B, the linear synchronous motor 324 may move the carrier 310 and diverted absorbent articles 102' along the track 312 to the drop off zone 316, where diverted absorbent articles 102' may be transferred from the receptacles 330 to the selective packing apparatus 318. It is to be appreciated that the diverted absorbent articles 102' may be transferred from the receptacles 330 in various ways, such as with a scraper bar.

In some configurations, it may be necessary to repetitively and rapidly decelerate, stop, and accelerate the carrier 310 while advancing through the receiving zone 314 and/or the drop off zone 316. For example, with reference to FIGS. 4A and 4B, the carrier 310 may be advanced in the transport direction TD through the receiving zone 314 to position an empty receptacle 330 at the downstream end or discharge end 340 of the second path 308 to receive a subsequently advancing diverted absorbent article 102'. When receiving diverted absorbent articles 102' being discharged from the second path 308 and assembly line 302 at a relatively high rate of speed, the carrier 310 may need to be accelerated, decelerated, stopped, and accelerated again very rapidly in order to properly position empty receptacles 330 at the discharge end 340 of the second path 308 at the proper times. Similarly, in the drop off zone 316, the carrier 310 may need to be accelerated, decelerated, stopped, and accelerated again very rapidly in order to properly position the diverted absorbent articles 102' at the selective packaging apparatus 318 at the proper times to allow for removal of the diverted absorbent articles 102' from the receptacles 330. In some instances, the linear synchronous motor 340 may not be able to exert the requisite motive forces on the carrier to accommodate the rapid acceleration and deceleration of the carrier 310 that may be required in the receiving zone 314 and/or the drop off zone 316. As such, the apparatus 300 may also include a drive mechanism 342 that selectively connects with the carrier 310 in the receiving zone 314 and/or the drop off zone 316. In turn, the drive mechanism 342 may apply forces to propel and stop the carrier 310 in the receiving zone 314 and/or drop off zone 316 at required acceleration and deceleration rates that the linear synchronous motor 324 alone may not be able to achieve.

Figure 4B:
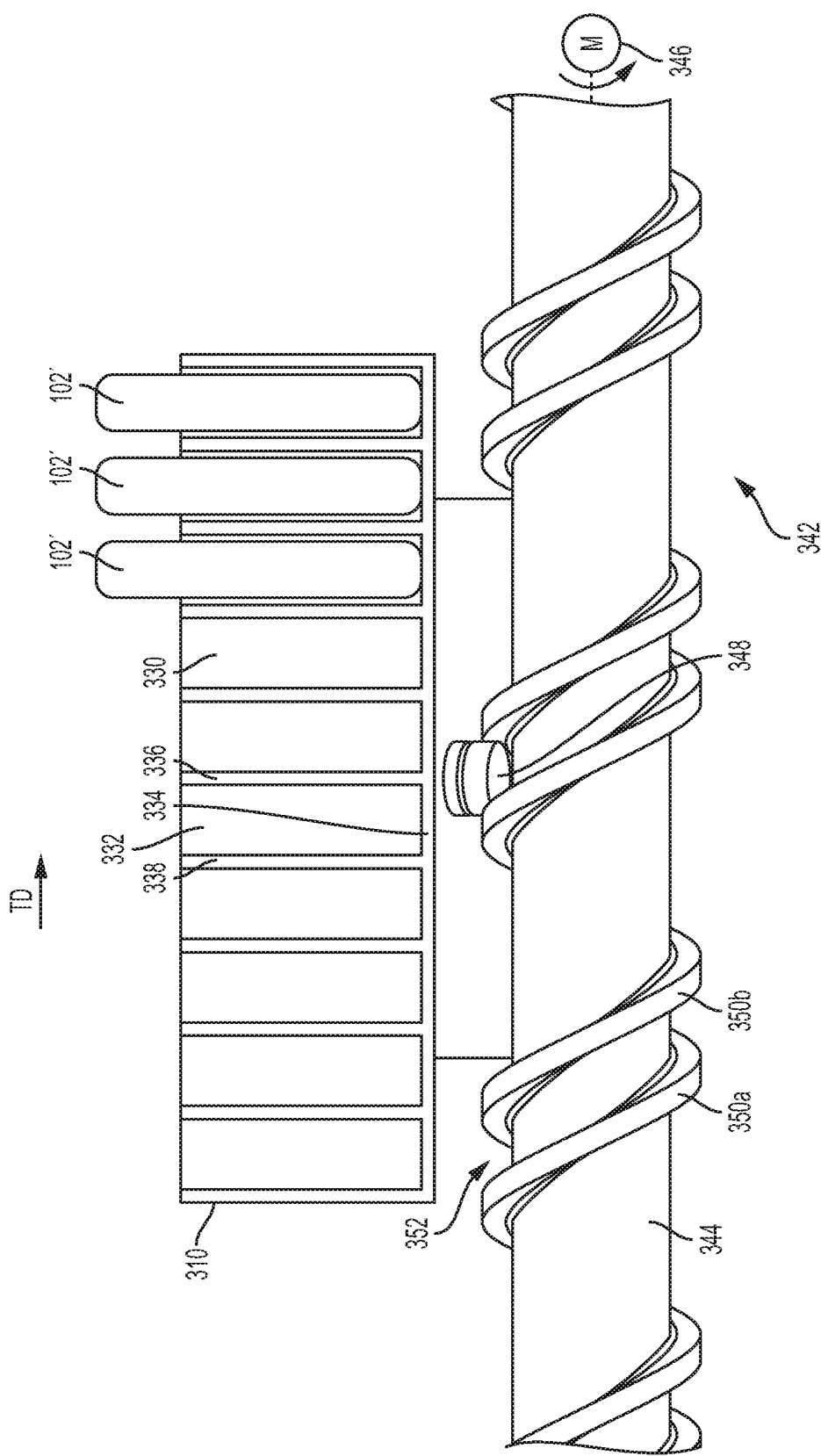
FIG. 4B is a detailed side schematic view of a drive mechanism adapted to advance the carrier through a receiving zone or a drop off zone.

It is to be appreciated that the drive mechanism 342 may be configured in various ways. For example, as shown in FIG. 4B, the drive mechanism 342 may include a drive member 344 rotatably driven by a motor 346. The drive member 344 may be configured as a screw that is threadedly engageable with the carrier 310 in the receiving zone 314 and/or the drop off zone 316. In some configurations, the carrier 310 may include follower member 348 that is adapted to threadedly connect with the drive member 344 in the receiving zone 314 and/or the drop off zone 316. As shown in FIG. 4B, the drive member 344 may include a first thread 350a and a second threads 350b extending helically around the drive member 344. The first thread 350a and second thread 350b may be separated from each other so as to define a channel 352 therebetween. Although the channel 352 may be defined by threads 350a, 350b protruding radially outward from the drive member 344, the channel 352 may be a defined by a helical path protruding radially inward into the drive member 344. In some configurations, the width of channel 352 may be constant or decrease along the length of the drive member in the transport direction TD. It is also to be appreciated that the drive mechanism may be configured to include two drive members 344 adapted to threadedly connect with two follower members 348 positioned on opposing sides of carrier 310. It is also to be appreciated that the drive member 344 may include more than one channel 352 adapted to engage multiple follower members 348 on the carrier 310.

When a carrier 310 advances into a receiving zone 314 and/or a drop zone 316, the follower member 348 may be received within the channel 352. As such, the motor 346 may intermittently rotate the drive member 344, causing the threads 350a, 35b to act on the follower member 348 to rapidly and repetitively accelerate, decelerate, stop, and re-accelerate the carrier 310 as the carrier 310 advances in the transport direction TD through a receiving zone 314 and/or a drop zone 316. Upon exiting the receiving zone 314 and/or drop zone 316, the drive mechanism 342 is disconnected from the carrier 310 as the follower member 348 is released from the channel 352. While the drive mechanism 342 is advancing the carrier 310, the motive forces applied to the carrier 310 from the linear synchronous motor 324 may be deactivated or remain activated in the receiving zone 314 and/or drop off zone 316.

It is to be appreciated that the apparatus 300 herein may be configured to operate in various ways to create select packages 106. For example, with reference to FIG. 2B, the apparatus 300 may include one or more carriers 310 movably connected with the track 312. The linear synchronous motor 324 advance the carriers 310 to the receiving zone 314. While in the receiving zone 314, the carriers 310 may be intermittently advanced to position the receptacles 330 to receive one or more diverted absorbent articles 102' advancing from the second path 308. Once the desired quantity of diverted absorbent articles 102' have been transferred to the carrier 310, the linear synchronous motor 324 may advance the carrier 310 and one or more diverted absorbent articles 102' to the drop off zone 316. While in the drop off zone 316, the carriers 310 may be intermittently advanced to position the receptacles 330 to have the one or more diverted absorbent articles 102' removed from the receptacles 330, such as with a scraper bar, and advanced to the selective packaging apparatus 318, wherein the one or more diverted absorbent articles 102' are placed into containers 104 to create select packages 106.

It is to be appreciated that one or more carriers 310 may advance through the receiving zone 314 and/or drop off zone 316 at the same time. In some configurations, the linear synchronous motor 324 may advance the one or more carriers 310 through the receiving zone 314 and/or drop off zone 316. In some configurations, the drive mechanism 342 may advance the one or more carriers 310 through the receiving zone 314 and/or drop off zone 316. It is also to be appreciated that diverted absorbent articles 102' may be packaged in various ways. For example, the apparatus 300 may be configured such that diverted absorbent articles 102' from a single carrier 310 may be positioned together in a single container 104, and in some configurations, diverted absorbent articles 102' from multiple carriers 310 may be positioned together in a single container 104.

Figure 5:
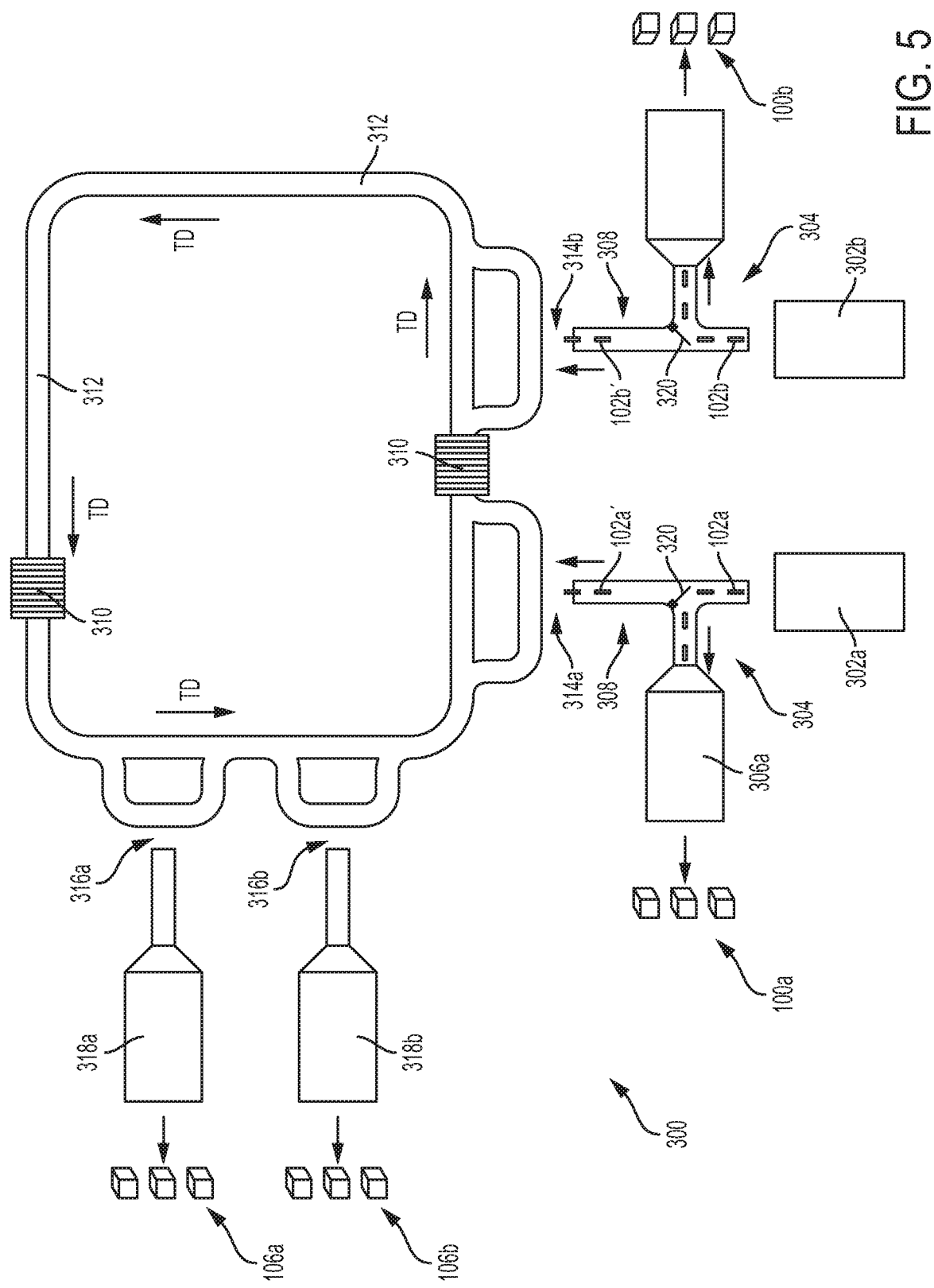
FIG. 5 is a schematic side view of a second configuration of an apparatus adapted to assemble select packages of absorbent articles.

It is also to be appreciated that the apparatus 300 may be configured operate with one or more assembly lines 302, and as such, may include more than one receiving zones 314 and/or more than one drop off zones 316. For example, as shown in FIG. 5, the apparatus 300 may include a first assembly line 302a and a second assembly line 302b. The first assembly line 302a may be adapted to assemble first absorbent articles 102a. And in one mode of operation, the first absorbent articles 102a may advance from the first assembly line 302a along a first path 304 toward a first packaging apparatus 306a, wherein the first packaging apparatus 306a may be configured to receive and place predetermined quantities of assembled first absorbent articles 102a into containers 104 as part of a mass production process to produce first packages 100a of first absorbent articles 102a. The second assembly line 302b may be adapted to assemble second absorbent articles 102b. And in one mode of operation, the second absorbent articles 102b may advance from the second assembly line 302b along a first path 304 toward a second packaging apparatus 306b, wherein the second packaging apparatus 306b may be configured to receive and place predetermined quantities of assembled second absorbent articles 102b into containers 104 as part of a mass production process to produce second packages 100b of second absorbent articles 102b.

In some configurations, the first absorbent articles 102a and the second absorbent articles 102b may comprise different features, such as for example, graphics, perfume scent, odor neutralizer, lotion, material construction, length, width, thickness, and/or absorbent capacity. In some configurations, the first absorbent articles 102a and the second absorbent articles 102b may be different types of absorbent articles, such as for example, sanitary napkins, panty liners, wound dressings, wipes, disposable diapers, adult incontinent diapers, adult incontinent pads, and adult incontinent pants. In some modes of operation, one or more first absorbent articles 102a may be diverted from a first path 304 from the first assembly line 302a to a second path 308 toward the first receiving zone 314a. And in some modes of operation, one or more second absorbent articles 102b may be diverted from a first path 304 from the second assembly line 302b to a second path 308 toward the second receiving zone 314b. As such, the apparatus 300 may be configured to operate in various ways to handle first absorbent articles 102a and second absorbent articles 102b to create a plurality of variations of select packages 106.

It is to be appreciated that one or more carriers 310 may be configured to advance through a single receiving zone 314 and/or may be configured to advance through a plurality of receiving zones 314. With reference to FIG. 5 for example, in some configurations, a first carrier 310 may receive only one or more diverted first absorbent articles 102a' in the first receiving zone 314a, and a second carrier 310 may receive only one or more diverted second absorbent articles 102b' in the second receiving zone 314b. In some configurations, one or more carriers 310 may receive one or more diverted first absorbent articles 102a' in the first receiving zone 314a and also may receive one or more diverted second absorbent articles 102b' in the second receiving zone 314b.

It is also to be appreciated that one or more carriers 310 may be configured to advance through a single drop off zone 316 and/or may be configured to advance through a plurality of drop off zones 316. With reference to FIG. 5 for example, in some configurations, a first carrier 310 may advance one or more diverted first absorbent articles 102a' to a first drop off zone 316a, wherein the diverted first absorbent articles 102a' are transferred to a first selective packaging apparatus 318a to create first select packages 106a. And a second carrier 310 may advance one or more diverted second absorbent articles 102b' to the second drop off zone 316b, wherein the diverted second absorbent articles 102b' are transferred to a second selective packaging apparatus 318b to create second select packages 106b.

In some configurations, a first carrier 310 may advance one or more diverted first absorbent articles 102a' to the first drop off zone 316a and to the second drop off zone 316b, wherein some diverted first absorbent articles 102a' are transferred to the first selective packaging apparatus 318a and some diverted first absorbent articles 102a' are transferred to the second selective packaging apparatus 318b. Similarly, a second carrier 310 may advance one or more diverted second absorbent articles 102b' to the first drop off zone 316a and to the second drop off zone 316b, wherein some diverted second absorbent articles 102b' are transferred to the first selective packaging apparatus 318a and some diverted second absorbent articles 102b' are transferred to the second selective packaging apparatus 318b. In turn, the first selective packaging apparatus 318a may create first select packages 106a of diverted first absorbent articles 102a' and diverted second absorbent articles 102b'. And the second selective packaging apparatus 318b may create second select packages 106b of diverted first absorbent articles 102a' and diverted second absorbent articles 102b'.

In yet other configurations, one or more carriers 310 may advance both diverted first absorbent articles 102a' and diverted second absorbent articles 102b' to the first drop off zone 316a and/or to the second drop off zone 316b. In turn, the first selective packaging apparatus 318a may create first select packages 106a of diverted first absorbent articles 102a' and/or diverted second absorbent articles 102b', and/or the second selective packaging apparatus 318b may create second select packages 106b of diverted first absorbent articles 102a' and/or diverted second absorbent articles 102b'.

Figure 6A:
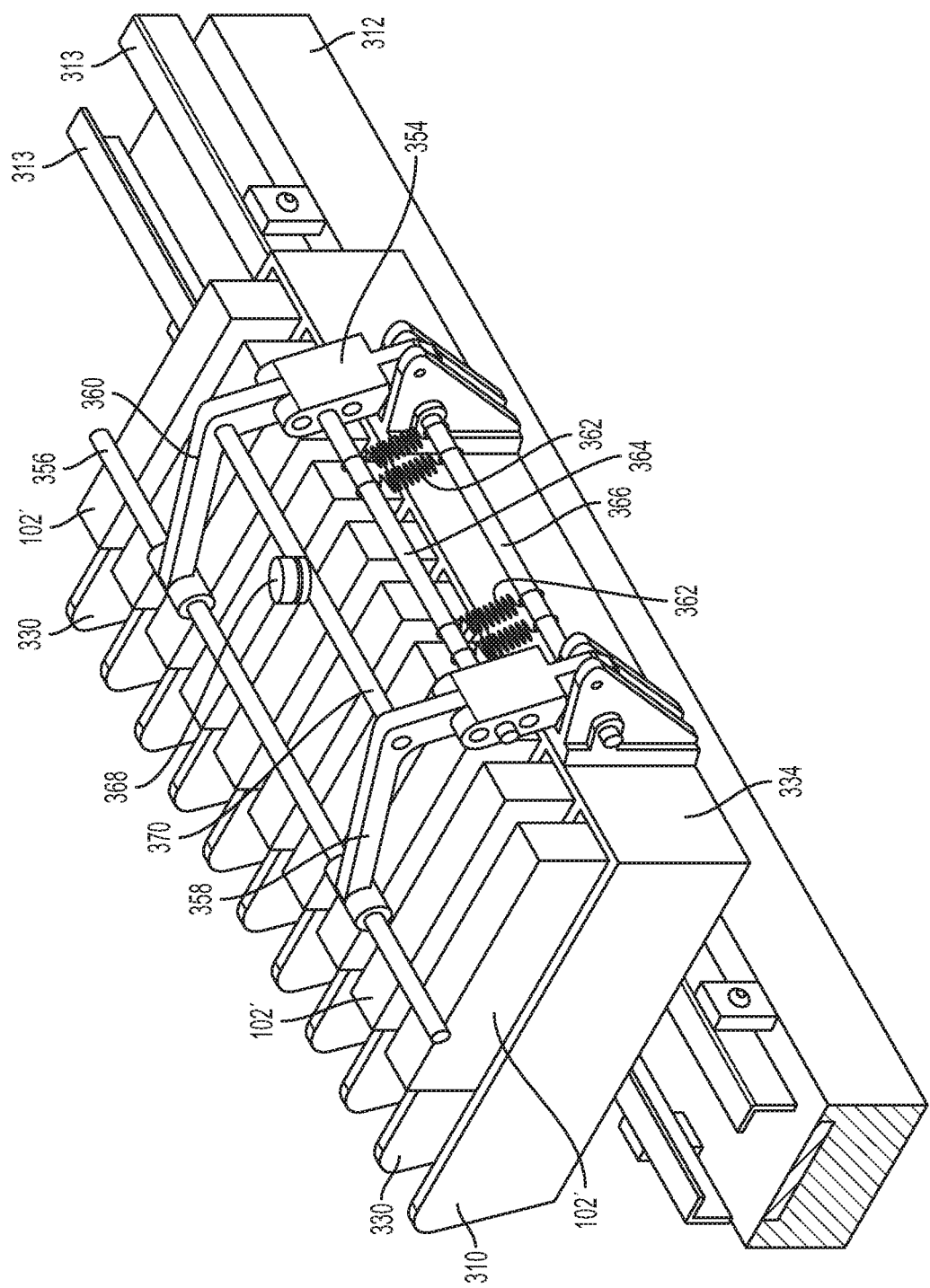
FIG. 6A is a view of a carrier including a restraining member.
Figure 6B:
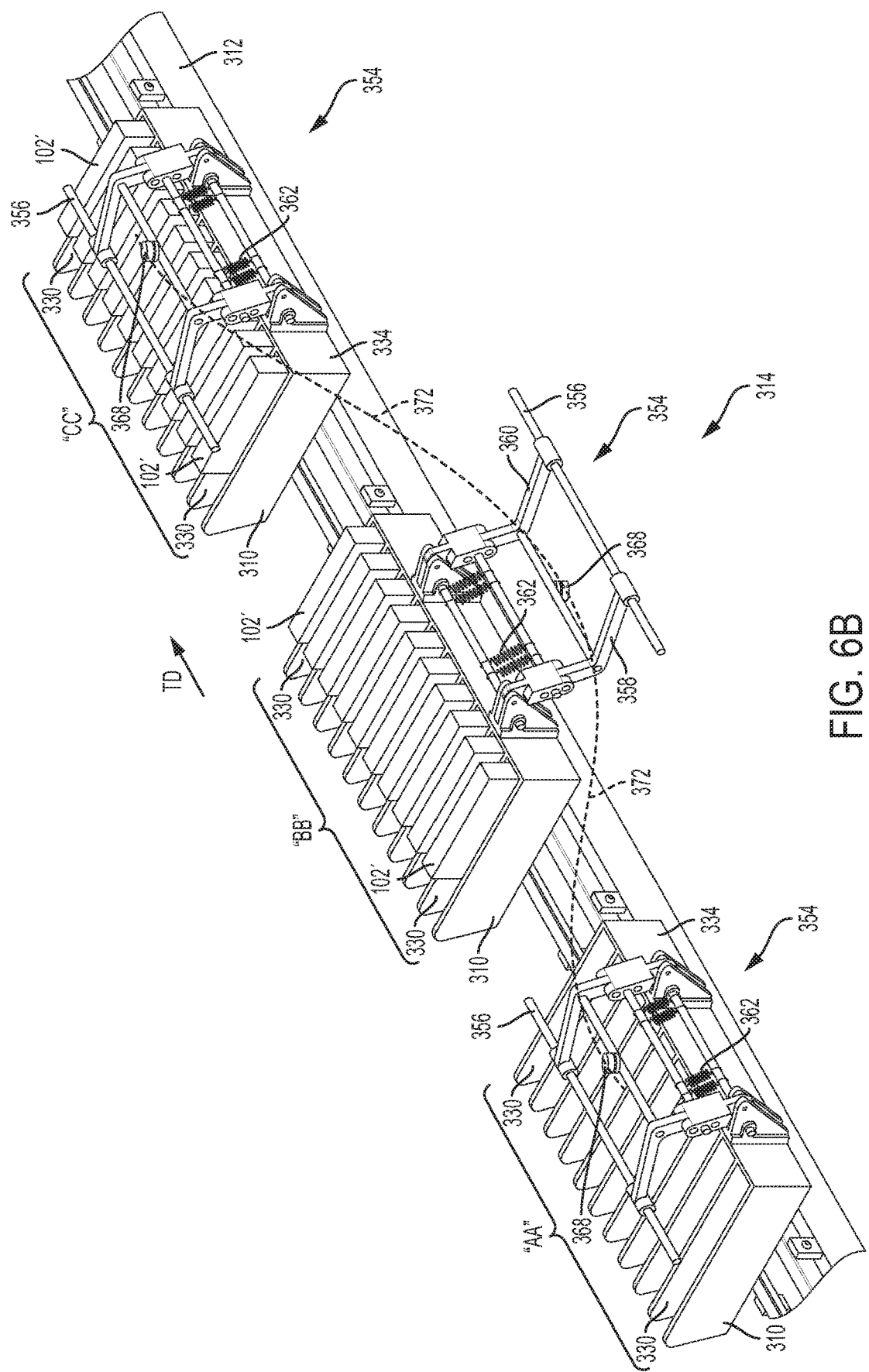
FIG. 6B is schematic view showing the operation of the restraining member as a carrier advances through a receiving zone.

It is also to be appreciated that the carriers 310 herein may be configured in various ways to transport various shapes and sizes of absorbent articles 102. In some configurations, the carrier 310 may be configured to transport relatively lightweight absorbent articles 102 at relatively high rates of speed. During periods of rapid acceleration, deceleration, and/or traveling along a turn in the track 312, absorbent articles 102 may be undesirably thrown from or misoriented on the carrier 310. As such, the carrier 310 may be configured to hold the absorbent articles 102 in position on the carrier 310 or in respective receptacles 330 while advancing along the track 312. For example, as shown in FIGS. 6A and 6B, the carriers 310 may include a restraining device 354 to help hold diverted absorbent articles 102' in a relatively fixed position on the carrier 310. The restraining device 354 may include a restraining member 356 connected with a first arm 358 and a second arm 360. As shown in FIG. 6A, the restraining member 356 may be connected with distal end portions of the first arm 358 and the second arm 360. And proximal end portions of the first arm 358 and the second arm 360 may be pivotally connected with the rear wall 334 of the receptacles 330. It is to be appreciated that the proximal end portions of the first arm 358 and the second arm 360 may be pivotally connected with various other portions of the carrier 330.

With continued reference to FIG. 6A, the restraining device 354 may also include one or more springs 362 connected between the first arm 358 and/or second arm 360 and the carrier 330. For example, a first cross member 364 may connect with central portions of the first arm 358 and the second arm 360, and a second cross member 366 may be connected with the rear wall 334 of the receptacles 330. In turn, springs 362 may be connected between the first cross member 364 and the second cross member 366. The springs 362 may be pre-loaded to exert tensile forces between the first cross member 364 and the second cross member 366 to cause the first arm 358 and the second arm 360 to pivot the restraining member 356 downward toward the receptacles 330. Thus, when diverted absorbent articles 102' are positioned in the receptacles 330, forces exerted from the springs 362 cause the restraining member 356 to push downward onto the diverted absorbent articles 102'. In turn, the downward forces of the restraining member 356 exerted on the diverted absorbent articles 102' help to hold the diverted absorbent articles 102' in relatively fixed positions on the carrier and in respective receptacles 330 while the carrier 310 is advancing along the track 312.

Depending on the designed configuration, the apparatus 300 may include additional features to help ensure that the restraining device 354 does not interfere with the transfer of diverted absorbent articles 102' to the carrier 310 in the receiving zone 314 and/or the transfer of diverted absorbent articles 102' from the carrier 310 in the drop off zone 316. For example, such as shown in FIG. 6A, the restraining device 354 may include a follower member 368 adapted to move the restraining member 356 upward and downward as the carrier 310 advances through the receiving zone 314 and/or the drop off zone 316. The follower member 368 may be connected with a third cross member 370 connected with and extending between the first arm 358 and the second arm 360. It is to be appreciated that the follower member 368 may be connected in various other ways and in various other locations.

FIG. 6B illustrates an example operation of the upward and downward movement of the restraining member 356 as the carrier 330 advances through a receiving zone 314. It is to be appreciated that a similar operation may be performed as the carrier 310 advances through a drop off zone 316. As the carrier 310 advances into the receiving zone 314 (and/or drop off zone 316) represented by "AA" in FIG. 6B, the follower member 368 may enter into or otherwise engage a cam track having a curved or helical shape generically represented with dashed line 372. With continued reference to FIG. 6B, as the follower member 368 advances along the curved cam track 372, the curved travel path of the follower member 368 causes the first arm 358 and second arm 360 to pivot and lift the restraining member 356 upward and away from the receptacles 330. While the restraining member is in an upward or lifted position, represented by "BB" in FIG. 6B, diverted absorbent articles 102' may be inserted into receptacles 330 in a receiving zone 314 (or removed from receptacles 330 in a drop off zone 316) without interference from the restraining member 356. As the carrier 310 advances in the transport direction TD past positions in the receiving zone 314 (or drop off zone 316) where diverted absorbent articles 102' may be inserted into (or removed from) receptacles 330, represented by "CC" in FIG. 6B, the curved travel path of the follower member 368 causes the first arm 358 and second arm 360 to pivot and move the restraining member 356 downward and toward the receptacles 330 and onto the diverted absorbent articles 102' (or empty receptacles 330). With continued advancement of the carrier 310, the follower member 368 exits or otherwise disengages the cam track 372 and the restraining member 356 is held in a downward position on diverted absorbent articles 102' and/or toward empty receptacles 330 with the spring forces as described above.

Figure 7:
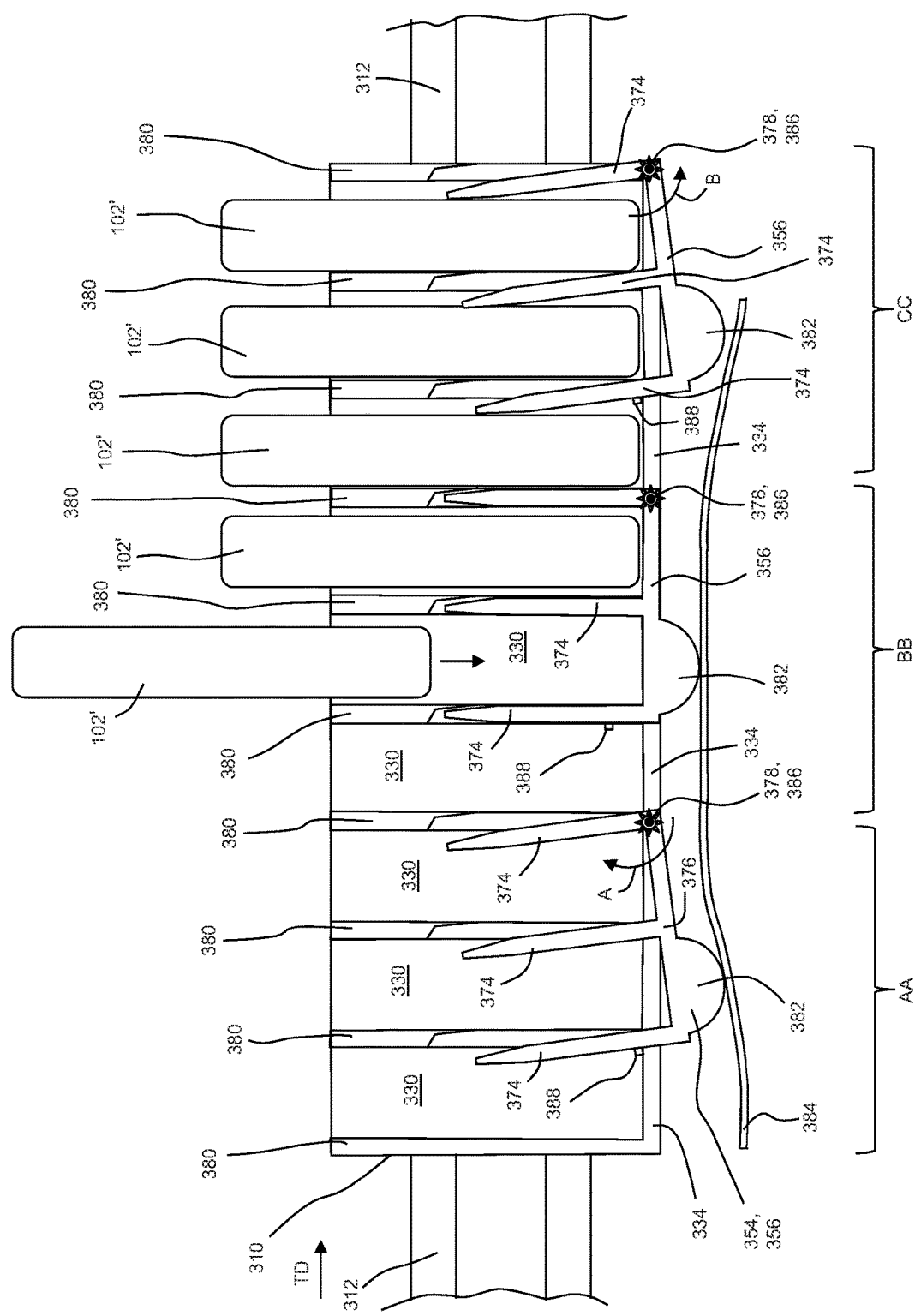
FIG. 7 is a detailed top schematic view showing the operation of a second embodiment of a restraining member as a carrier advances through a receiving zone.

It is also to be appreciated that restraining devices 354 may be configured in various ways to help hold diverted absorbent articles 102' in relatively fixed positions on the carrier 310. For example, FIG. 7 shows a top view of a carrier 310 including a second configuration of a restraining device 354 that may include one or more restraining members 356 pivotally connected with the carrier 310. Although the carrier 310 shown in FIG. 7 is illustrated with three restraining members 356, it is to be appreciated that the carrier may be configured with more or less than three restraining members 356.

As shown in FIG. 7, each restraining member 356 may be configured as a forked shaped member including a plurality of tine or finger members 374 extending from a base member 376. In turn, the base member 376 may be pivotally connected with the rear wall 334 of the carrier 310 and adapted to pivot about an axis 378. The tine members 374 may be spaced apart from each other by a distance that is equal to or approximately equal to the distance by which sidewalls 380 of the receptacles 330 of the carrier 310 are spaced apart from each other. The sidewalls 380 may be configured similar to the sidewalls 336, 338 discussed above.

Depending on the designed configuration, the apparatus 300 may include additional features to help ensure that the tine members 374 do not interfere with the transfer of diverted absorbent articles 102' to the carrier 310 in the receiving zone 314 and/or the transfer of diverted absorbent articles 102' from the carrier 310 in the drop off zone 316. For example, such as shown in FIG. 7, the restraining device 354 may include a follower 382 adapted to contact a guide member 384. As discussed below, the guide member 384 may be shaped to cause the restraining member 356 to pivot about the axis 378 in direction "A" as the carrier 310 moves along a travel direction TD through the receiving zone 314 and/or the drop off zone 316. It is to be appreciated that the follower 382 may be connected in various other ways and in various other locations.

With continued reference to FIG. 7, the restraining device 354 may also include a spring 386, such as a torsional spring, connected between the carrier 310 and the restraining member 356 that is biased to exert forces that cause the restraining member 356 to pivot about the axis 378 in direction "B". Thus, when diverted absorbent articles 102' are positioned in the receptacles 330, forces exerted from the spring 386 cause the restraining member 356 to pivot in direction "B", which in turn, causes the tine members 374 to push diverted absorbent articles 102' against an opposing sidewall 380 of the receptacle 330. In turn, the forces exerted on the diverted absorbent articles 102' by the tine members 374 help to hold the diverted absorbent articles 102' in relatively fixed positions on the carrier 310 and in respective receptacles 330 while the carrier 310 is advancing along the track 312. The restraining member 356 may also include a stop member 388 that is adapted to contact the rear wall 334 of the carrier 356 to limit the amount by which the restraining member 356 may rotate in direction "B".

FIG. 7 also illustrates an example operation of the pivotal movement of the restraining member 356 as the carrier 330 advances through a receiving zone 314. It is to be appreciated that a similar operation may be performed as the carrier 310 advances through a drop off zone 316. As the carrier 310 advances into the receiving zone 314 (and/or drop off zone 316) represented by "AA" in FIG. 7, the follower 382 may contact or otherwise engage the guide member having a curved portion. With continued reference to FIG. 7, as the follower 382 advances along the curved portion of the guide member 384, the corresponding travel path of the follower 382 causes the restraining member 356 to pivot in direction "A" and position the tine members 374 into alignment with the sidewalls 380 of the receptacles 330. While the tine members 374 are in the aligned position, represented by "BB" in FIG. 7, diverted absorbent articles 102' may be inserted into receptacles 330 in a receiving zone 314 (or removed from receptacles 330 in a drop off zone 316) without interference from the restraining member 356. As the carrier 310 advances in the transport direction TD past positions in the receiving zone 314 (or drop off zone 316) where diverted absorbent articles 102' may be inserted into (or removed from) receptacles 330, represented by "CC" in FIG. 7, the follower 382 may advance along a reversed sloped portion of the guide member 384 and/or may disengage from the guide member 384, wherein the spring 386 causes the restraining member 354 to pivot in direction "B" and move the tine members 374 into contact with the diverted absorbent articles 102'. With continued advancement of the carrier 310, diverted absorbent articles 102' are held in position in the receptacles between the tine members 374 and corresponding sidewalls 380 with the spring forces as described above. It is to be appreciated that the guide member 384 may comprise various different shapes and sizes than what is illustrated in FIG. 7.

This application claims the benefit of U.S. Provisional Application No. 62/655,266, filed on Apr. 10, 2018, the entirety of which is incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for flexibly producing packages of absorbent articles, the method comprising:
   providing carriers movably connected with a track;
   assembling absorbent articles with two or more assembly lines, wherein each assembly line produces absorbent articles having different features, and wherein each assembly line is connected to the track;
   advancing the absorbent articles from each of the two or more assembly lines along first paths toward first dedicated packaging apparatus;
   diverting an absorbent articles from the first paths to second paths prior to the first dedicated packaging apparatus;
   advancing the diverted absorbent article along the second paths;
   transferring the diverted absorbent articles from the second paths to the carriers in receiving zones;
   moving the carriers along the track with a linear synchronous motor from the receiving zones to a drop off zone; and
   transferring the diverted absorbent articles from the carriers in the drop off zone to a second packaging apparatus wherein the second packaging apparatus is able to receive absorbent articles from each of the two or more assembly lines.

2. The method of claim 1, further comprising:
   moving the carrier along the track with the linear synchronous motor from the drop off zone to the receiving zone;
   connecting the carrier with a drive mechanism upon entering the receiving zone;
   moving the carrier through the receiving zone with the drive mechanism;
   intermittently accelerating and decelerating the carrier on the track with the drive mechanism through the receiving zone; and
   disconnecting the drive mechanism from the carrier upon exiting the receiving zone.

3. The method of claim 2, further comprising the step of deactivating motive forces applied to the carrier from the linear synchronous motor in the receiving zone.

4. The method of claim 2, wherein the drive mechanism comprises a screw rotatably driven by a motor and threadedly engageable with the carrier.

5. The method of claim 1, further comprising holding the diverted absorbent articles on the carrier with a restraining member.

6. The method of claim 1, further comprising:
   connecting the carrier with a drive mechanism upon entering the drop off zone;

moving the carrier through the drop off zone with the drive mechanism;

intermittently accelerating and decelerating the carrier on the track with the drive mechanism through the drop off zone; and disconnecting the drive mechanism from the carrier upon exiting the drop off zone.

7. The method of claim 1, wherein the linear synchronous motor comprises a coil connected with the track and a permanent magnet connected with the carrier.

8. The method of claim 7, further comprising slowing carrier by creating eddy currents in the track with the permanent magnet.

9. The method of claim 1, wherein the carrier comprises wheels rollingly engaged with the track.

10. The method of claim 1, wherein the different features of the diverted absorbent article and the second absorbent article are selected from the group consisting of: graphics, perfume scent, odor neutralizer, lotion, material construction, length, width, thickness, and absorbent capacity.

11. The method of claim 10, wherein the diverted absorbent article and the second absorbent article comprise absorbent articles selected from the group consisting of: sanitary napkins, panty liners, wound dressings, wipes, disposable diapers, adult incontinent diapers, adult incontinent pads, and adult incontinent pants.

12. A method for flexibly producing packages of absorbent articles, the method comprising:

providing a first carrier and a second carrier movably connected with a track, wherein the first and second carriers are independently driven along the track with a linear synchronous motor;

assembling first absorbent articles with a first assembly line and assembling second absorbent articles with a second assembly line; wherein the first and second assembly lines are connected to the track and wherein the first absorbent articles and second absorbent articles comprise different features;

advancing the first absorbent articles from the first assembly line along a first path toward a first dedicated packaging apparatus;

advancing the second absorbent articles from the second assembly line along a second path toward a second dedicated packaging apparatus;

diverting a first absorbent article from the first path prior to the first dedicated packaging apparatus to the first carrier in a first receiving zone;

diverting a second absorbent article from the second path prior to the second dedicated packaging apparatus to the second carrier in a second receiving zone;

moving the first carrier with the diverted first absorbent article along the track with the linear synchronous motor from the first receiving zone to a drop off zone;

moving the second carrier with the diverted second absorbent article along the track with the linear synchronous motor from the second receiving zone to the drop off zone;

transferring the diverted first absorbent article from the first carrier and the diverted second absorbent article from the second carrier in the drop off zone to a third packaging apparatus to place the diverted first absorbent article and the diverted second absorbent article together in a package.

13. The method of claim 12, wherein the different features are selected from the group consisting of: graphics, perfume scent, odor neutralizer, lotion, material construction, length, width, thickness, and absorbent capacity.

14. The method of claim 12, wherein the first and second absorbent articles comprise absorbent articles selected from the group consisting of: sanitary napkins, panty liners, wound dressings, wipes, disposable diapers, adult incontinent diapers, adult incontinent pads, and adult incontinent pants.

15. The method of claim 12, further comprising:

moving the first carrier along the track with the linear synchronous motor from the drop off zone to the first receiving zone;

connecting the first carrier with a first drive mechanism upon entering the first receiving zone;

moving the first carrier through the first receiving zone with the first drive mechanism;

intermittently accelerating and decelerating the first carrier on the track with the first drive mechanism through the first receiving zone; and disconnecting the first drive mechanism from the first carrier upon exiting the first receiving zone.

16. The method of claim 15, further comprising:

connecting the first carrier and the second carrier with a second drive mechanism upon entering the drop off zone;

moving the first carrier and the second carrier through the drop off zone with the second drive mechanism;

intermittently accelerating and decelerating the first carrier and the second carrier on the track with the second drive mechanism through the drop off zone; and disconnecting the second drive mechanism from the first carrier and the second carrier upon exiting the drop off zone.

17. A method for flexibly producing packages of absorbent articles, the method comprising:

providing a carrier movably connected with a track;

assembling first absorbent articles with a first assembly line and assembling second absorbent articles with a second assembly line, wherein the first absorbent articles and second absorbent articles comprise different features;

advancing the first absorbent articles from the first assembly line along a first path toward a first dedicated packaging apparatus;

advancing the second absorbent articles from the second assembly line along a second path toward a second dedicated packaging apparatus;

diverting a first absorbent article from the first path prior to the first dedicated packaging apparatus;

transferring the diverted first absorbent article from the first path to the carrier in a first receiving zone;

moving the carrier and the diverted first absorbent article along the track with a linear synchronous motor from the first receiving zone to a second receiving zone;

diverting a second absorbent article from the second path prior to the second dedicated packaging apparatus;

transferring the diverted second absorbent article from the second path to the carrier in the second receiving zone;

moving the carrier with the diverted first and second absorbent articles along the track with the linear synchronous motor from the second receiving zone to a drop off zone; and transferring the diverted first absorbent article and the diverted second absorbent article from the carrier in the drop off zone to a third packaging apparatus to place the diverted first absorbent article and the diverted second absorbent article together in a package.

18. The method of claim 17, wherein the different features are selected from the group consisting of: graphics, perfume scent, odor neutralizer, lotion, material construction, length, width, thickness, and absorbent capacity.

19. The method of claim 17, wherein the first and second absorbent articles comprise absorbent articles selected from the group consisting of: sanitary napkins, panty liners, wound dressings, wipes, disposable diapers, adult incontinent diapers, adult incontinent pads, and adult incontinent pants.

20. The method of claim 17, further comprising:
moving the carrier along the track with the linear synchronous motor from the drop off zone to the first receiving zone;
connecting the carrier with a first drive mechanism upon entering the first receiving zone;
moving the carrier through the first receiving zone with the first drive mechanism;
intermittently accelerating and decelerating the carrier on the track with the first drive mechanism through the first receiving zone; and
moving the carrier along the track with the linear synchronous motor from the first receiving zone to the second receiving zone connecting the carrier with a second drive mechanism upon entering the second receiving zone;
moving the carrier through the second receiving zone with the second drive mechanism;
intermittently accelerating and decelerating the carrier on the track with the second drive mechanism through the second receiving zone
disconnecting the second drive mechanism from the first carrier upon exiting the second receiving zone.

* * * * *